United States Patent
Doudkine et al.

(10) Patent No.: US 11,938,268 B2
(45) Date of Patent: Mar. 26, 2024

(54) CPAP SYSTEM

(71) Applicant: ResMed Pty Ltd, Bella Vista (AU)

(72) Inventors: Dmitri Anatolievich Doudkine, Sydney (AU); Siyin Wong, Sydney (AU)

(73) Assignee: ResMed Pty, Ltd., Bella Vista (AU)

( * ) Notice: Subject to any disclaimer, the term of this patent is extended or adjusted under 35 U.S.C. 154(b) by 1015 days.

(21) Appl. No.: 16/850,703

(22) Filed: Apr. 16, 2020

(65) Prior Publication Data

US 2020/0330717 A1  Oct. 22, 2020

Related U.S. Application Data

(60) Provisional application No. 62/897,558, filed on Sep. 9, 2019, provisional application No. 62/835,094, filed on Apr. 17, 2019.

(51) Int. Cl.
*A61M 16/00*  (2006.01)
*A61M 16/08*  (2006.01)
(Continued)

(52) U.S. Cl.
CPC ...... *A61M 16/024* (2017.08); *A61M 16/0066* (2013.01); *A61M 16/022* (2017.08); (Continued)

(58) Field of Classification Search
CPC .............. A61M 16/107; A61M 16/108; A61M 16/1085; A61M 16/109; A61M 16/1095; (Continued)

(56) References Cited

U.S. PATENT DOCUMENTS 4,782,832 A  11/1988  Trimble et al.
4,944,310 A   7/1990  Sullivan
(Continued)

FOREIGN PATENT DOCUMENTS

WO  WO 98/004310 A1  2/1998
WO  WO 98/034665 A1  8/1998
(Continued)

OTHER PUBLICATIONS

"*Respiratory Physiology*", by John B. West, Lippincott Williams & Wilkins, $9^{th}$ edition published 2012 (8 pages).

*Primary Examiner* — Elliot S Ruddie
*Assistant Examiner* — Maap Ahmed Ellabib
(74) *Attorney, Agent, or Firm* — Nixon & Vanderhye, P.C.

(57) ABSTRACT

An apparatus for providing a supply of humidified pressurized breathable gas to a patient interface, the apparatus comprising: a flow generator configured to pressurize a supply of breathable gas; a humidifier configured to provide water vapour to humidify the supply of pressurized breathable gas; a heated tube configured to be connectable to the humidifier to heat and deliver the humidified supply of breathable gas to the patient interface; a sensor configured to measure a property of the humidified supply of breathable gas in the heated tube; a controller configured to control power provided to the heated tube and control operation of the flow generator; and a set of low pass filters coupled between the sensor and the controller and/or a set of high pass filters coupled between the sensor and ground.

17 Claims, 22 Drawing Sheets

(51) Int. Cl.
*A61M 16/10* (2006.01)
*A61M 16/16* (2006.01)

(52) U.S. Cl.
CPC ...... *A61M 16/0816* (2013.01); *A61M 16/107* (2014.02); *A61M 16/108* (2014.02); *A61M 16/1085* (2014.02); *A61M 16/109* (2014.02); *A61M 16/1095* (2014.02); *A61M 16/16* (2013.01); *A61M 16/161* (2014.02); *A61M 2016/0027* (2013.01); *A61M 2016/0039* (2013.01); *A61M 16/0875* (2013.01); *A61M 2205/0233* (2013.01); *A61M 2205/15* (2013.01); *A61M 2205/3653* (2013.01); *A61M 2205/3673* (2013.01); *A61M 2207/00* (2013.01)

(58) Field of Classification Search
CPC ............ A61M 16/161; A61M 16/0875; A61M 2016/0027; A61M 2016/0039; A61M 2205/0233; A61M 2205/15; A61M 2205/3653; A61M 2205/3673; A61M 2207/00
USPC ......................................... 330/10, 207 A, 251
See application file for complete search history.

(56) References Cited

U.S. PATENT DOCUMENTS

| | | |
|---|---|---|
| 5,411,474 A | 5/1995 | Ott et al. |
| 5,454,061 A | 9/1995 | Carlson |
| 6,532,959 B1 | 3/2003 | Berthon-Jones |
| 6,581,594 B1 | 6/2003 | Drew et al. |
| 6,598,604 B1 | 7/2003 | Seakins |
| 6,953,354 B2 | 10/2005 | Edirisuriya et al. |
| 7,866,944 B2 | 1/2011 | Kenyon et al. |
| 8,186,345 B2 * | 5/2012 | Payton .............. A61M 16/0875 261/DIG. 65 |
| 8,453,641 B2 | 6/2013 | Payton et al. |
| 8,636,479 B2 | 1/2014 | Kenyon et al. |
| 8,638,014 B2 | 1/2014 | Sears et al. |
| 8,733,349 B2 | 5/2014 | Bath et al. |
| 9,265,902 B2 | 2/2016 | Payton et al. |
| 9,572,949 B2 | 2/2017 | Vos et al. |
| 9,987,455 B2 | 6/2018 | Stoks et al. |
| 10,086,158 B2 | 10/2018 | Bath et al. |
| 10,143,821 B2 | 12/2018 | Pujol, Jr. |
| 2009/0044808 A1 | 2/2009 | Guney Memduh et al. |
| 2009/0050156 A1 | 2/2009 | Ng et al. |
| 2010/0000534 A1 | 1/2010 | Kooij et al. |
| 2011/0120462 A1 * | 5/2011 | Tatkov ................ A61M 16/161 128/203.14 |
| 2015/0101600 A1 | 4/2015 | Miller et al. |
| 2016/0354573 A1 | 12/2016 | Buswell et al. |
| 2018/0200470 A1 | 7/2018 | Dixon et al. |
| 2018/0280652 A1 | 10/2018 | Sims |

FOREIGN PATENT DOCUMENTS

| | | |
|---|---|---|
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2009/052560 A1 | 4/2009 |
| WO | WO 2010/135785 A1 | 12/2010 |
| WO | WO 2012/171072 A1 | 12/2012 |
| WO | WO 2013/020167 A1 | 2/2013 |
| WO | WO 2014142679 | 9/2014 |
| WO | WO 2018116187 | 6/2018 |

* cited by examiner

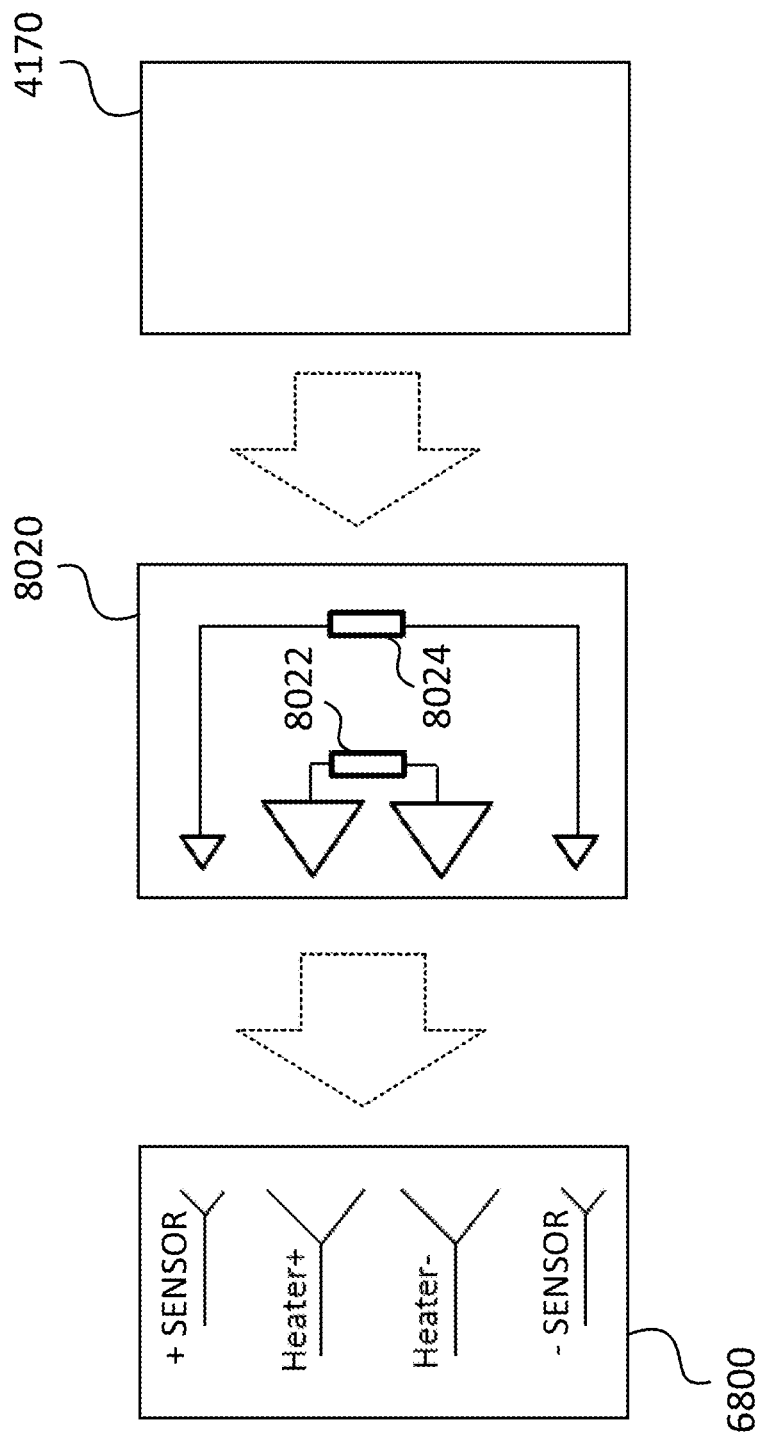

CPAP SYSTEM

1 CROSS-REFERENCE TO RELATED APPLICATIONS

This application claims the benefit of U.S. Provisional Application No. 62/835,094, filed Apr. 17, 2019, and of U.S. Provisional Application No. 62/897,558, filed Sep. 9, 2019, each of which is incorporated herein by reference in its entirety.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
|---|---|---|
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

An aspect of one form of the present technology is a method of manufacturing apparatus.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

Another aspect of the present technology relates to a CPAP system including a humidifier, a patient interface, and an air delivery tube to deliver humidified air to the patient interface. In an example, the humidifier is integrated with an RPT device structured to produce a flow of air at positive pressure.

Another aspect of the present technology relates to including one or more filters coupled to a sensor circuit at least partially disposed in an air delivery tube for sensing temperature changes in an air delivery tube.

In examples, the one or more filters may be configured to filter pulse frequencies of a PWM signal applied to one or more heating elements in the air delivery tube; the one or more filters include one or more high pass filters; and/or the one or more filters include one or more low pass filters.

Another aspect of the present technology relates to an apparatus for providing a supply of humidified pressurized breathable gas to a patient interface. The apparatus includes a flow generator configured to pressurize a supply of breathable gas, a humidifier configured to provide water vapour to humidify the supply of pressurized breathable gas, a heated tube configured to be connectable to the humidifier to heat and deliver the humidified supply of breathable gas to the patient interface, a sensor circuit configured to measure a property of the humidified supply of breathable gas in the heated tube, a controller configured to control power provided to the heated tube and control operation of the flow generator, and one or more filters coupled to the sensor circuit.

In examples, the one or more filters may be configured to filter pulse frequencies of a PWM signal applied to one or more heating elements in the air delivery tube; the one or more filters include one or more high pass filters; the one or more filters include one or more low pass filters; the one or more filters include a set of low pass filters coupled between the sensor circuit and the controller; and/or the one or more filters include a set of high filters coupled between the sensor circuit and ground.

Another aspect of the present technology relates to including one or more low pass filters and/or one or more high pass filters coupled to a sensor circuit at least partially disposed in an air delivery tube for sensing temperature changes in the air delivery tube. The filters may be configured to filter pulse frequencies of a PWM signal applied to one or more heating elements in the air delivery tube.

Another aspect of the present technology relates to including one or more low pass filters and/or one or more high pass filters coupled to a sensor circuit at least partially disposed in an air delivery tube for sensing temperature changes in the air delivery tube, wherein a sensing signal is applied periodically to the sensor circuit.

Another aspect of the present technology relates to including a first low pass filter coupled to one end of a sensor included in an air delivery tube and a second low pass filter coupled to a second end of the sensor, wherein a sensing signal is applied at predetermined intervals to the sensor for sensing temperature changes in the air delivery tube.

Another aspect of the present technology relates to including a first high pass filter coupled to one end of a sensor included in an air delivery tube and a second high pass filter coupled to a second end of the sensor, wherein a sensing signal is applied at predetermined intervals to the sensor for sensing temperature changes in the air delivery tube. The first and second high pass filters may be coupled between the sensor and ground.

Another aspect of the present technology relates to including a first low pass filter coupled to a first output of a divider network for detecting operating parameters of a sensor disposed in an air delivery tube and a second low pass filter coupled to a second output of the divider network.

Another aspect of the present technology relates to including a first high pass filter coupled to a first output of a divider network for detecting operating parameters of a sensor disposed in an air delivery tube and a second high pass filter coupled to a second output of the divider network. The first and second high pass filters may be coupled between the sensor and ground.

Another aspect of the present technology relates to an apparatus for providing a supply of humidified pressurized breathable gas to a patient interface. The apparatus includes a flow generator configured to pressurize a supply of breathable gas, a humidifier configured to provide water vapour to humidify the supply of pressurized breathable gas, a heated tube configured to be connectable to the humidifier to heat and deliver the humidified supply of breathable gas to the patient interface, a sensor configured to measure a property of the humidified supply of breathable gas in the heated tube, a controller configured to control power provided to the heated tube and control operation of the flow generator, and a set of low pass filters coupled between the sensor and the controller and/or a set of low high filters coupled between the sensor and ground.

In examples, the apparatus can include one or more of the following features: (a) the apparatus comprises two high pass filters, one connected between each respective terminal of the sensor and the ground; (b) the apparatus comprises a set of low pass filters coupled between the sensor and the controller and the set of high pass filters coupled between the sensor and the ground; (c) the power supplied to the heated tube comprises a pulse width modulated power signal and at least a set of low pass filters is configured to filter frequencies near the frequencies of the pulse width modulated power signal and frequencies higher than the frequencies of the pulse width modulated power signal; (d) the sensor is coupled to a sensor power source, wherein the controller is configured to: control the sensor power source to provide intermittently power to the sensor in order to detect a connection of the heated tube; and keep the sensor power source on, when it is detected that the heated tube is connected to the humidifier; (e) includes the set of low pass filters, each low pass filter including an active component; (f) includes the set of high pass filters, each including an active component; (g) the heated tube includes a set of sensor wires extending along the length of the heated tube, each of the sensor wires coupled to the sensor and the controller; (h) includes the set of high pass filters, wherein a first high pass filter of the set of high pass filters is coupled between ground and one of the sensor wires, and a second high pass filter of the set of high pass filters is coupled between ground and another one of the sensor wires; (i) includes the set of low pass filters, wherein a first low pass filter of the set of low pass filters is coupled between the controller and one of the sensor wires, and a second low pass filter of the set of low pass filters is coupled between the controller and another one of the sensor wires; (j) the controller includes a sensing circuit configured to detect voltage and/or current changes, and the controller is configured to control power provided to the heated tube based on the detected voltage and/or current changes; (k) the heated tube includes a pair of helically wound heating wires around an axis of the heated tube and extending along the length of the heated tube, configured to heat air in the heated tube, and coupled to ground and a heater control circuit included in the controller; (l) includes the set of high pass filters, wherein the heated tube includes a set of sensor wires extending along the length of the heated tube, each of the sensor wires coupled to the sensor and the controller, and a first high pass filter of the set of high pass filters is coupled between the ground and one of the sensor wires, and a second high pass filter of the set of high pass filters is coupled between the ground and another one of the sensor wires; (m) includes the set of high pass filters, wherein the set of high pass filters is provided in the heated tube; (n) includes the set of low pass filters, wherein the set of low pass filters is provided in the heated tube; and/or (o) includes the set of low pass filters, wherein the set of low pass filters is provided outside of the heated tube.

Another aspect of the present technology relates to an apparatus for treating a respiratory disorder in a patient, the apparatus comprising: a motor-blower configured to generate a supply of air at a positive pressure relative to ambient pressure; a humidifier configured to provide water vapour to humidify the supply of pressurized air; a tube removably connected to the humidifier on one end and a patient interface on another end, the tube including one or more heating wires extending along the length of the tube and configured to heat the humidified supply of breathable air passed though the tube and one or more sensor wires extending along the length of the tube and coupled to a sensor configured to measure a property of the humidified supply of breathable gas in the tube; a controller including circuitry configured to control power provided to the one or more heating wires, control operation of the motor-blower, and control operation of the humidifier; and one or more high pass filters coupled between the one or more sensor wires and ground.

In examples, the apparatus can include one or more of the following features: (a) further comprising one or more low pass filters coupled between the one or more sensor wire and the controller; (b) the apparatus comprises two heating wires, two sensor wires, a set of low pass filters coupled between the sensor wires and the controller, and a set of high pass filters coupled between the sensor wire and the ground; and/or (c) the power provided to the heating wires comprises a pulse width modulated power signal and the one or more low pass filters are configured to filter frequencies near the frequencies of the pulse width modulated power signal and frequencies higher than the frequencies of the pulse width modulated power signal.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing. Moreover, the described methods, systems, devices and apparatus can provide improvements in measurements of signals from sensors.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device 4000 is humidified in a humidifier 5000, and passes along an air circuit 4170 to the patient 1000. The patient is sleeping in a side sleeping position.

4.2 Respiratory System and Facial Anatomy

4.3 Patient Interface

Figure 3:
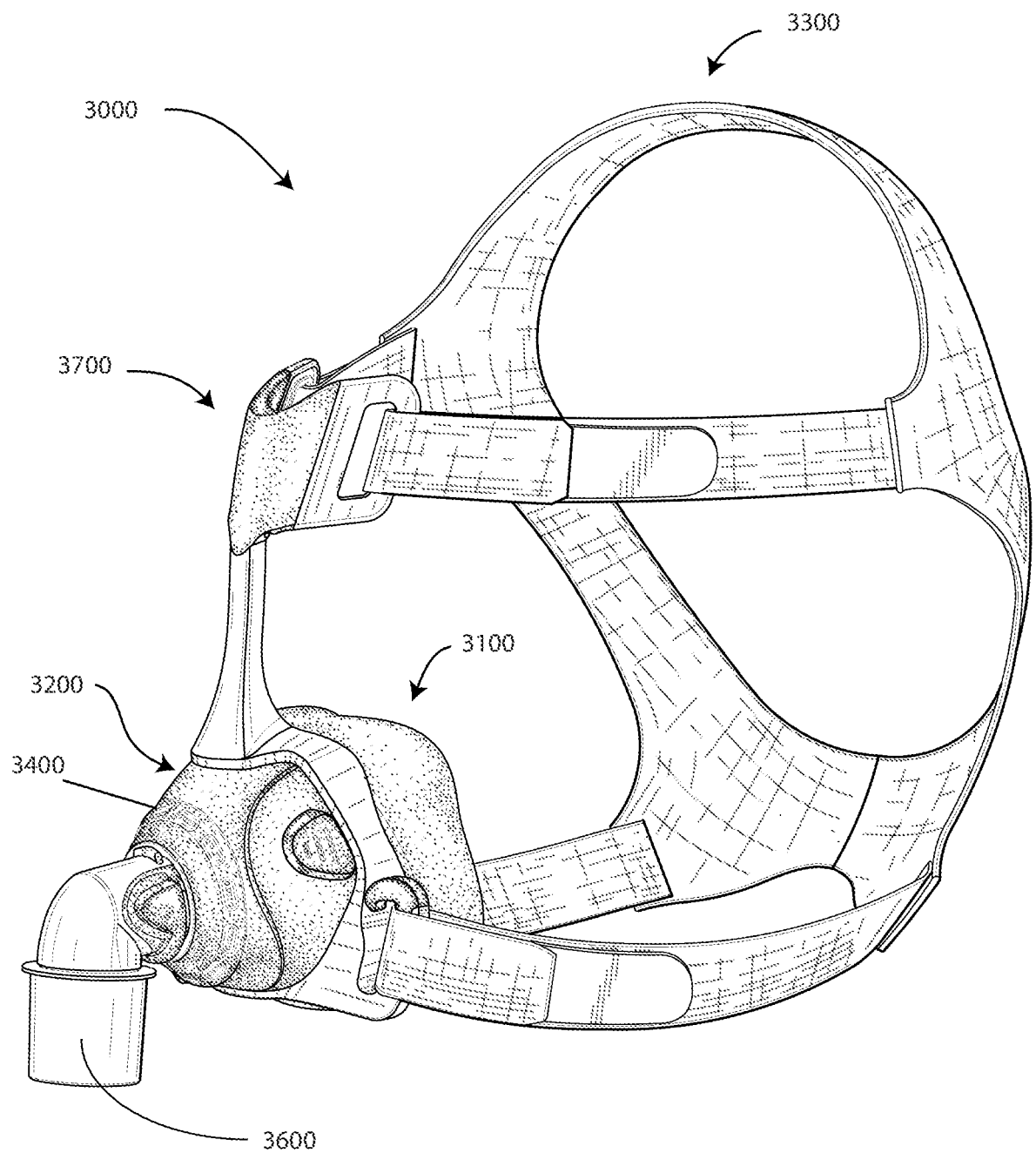

FIG. 3 shows a patient interface in the form of a nasal mask in accordance with one form of the present technology.

4.4 Breathing Waveforms

Figure 4:
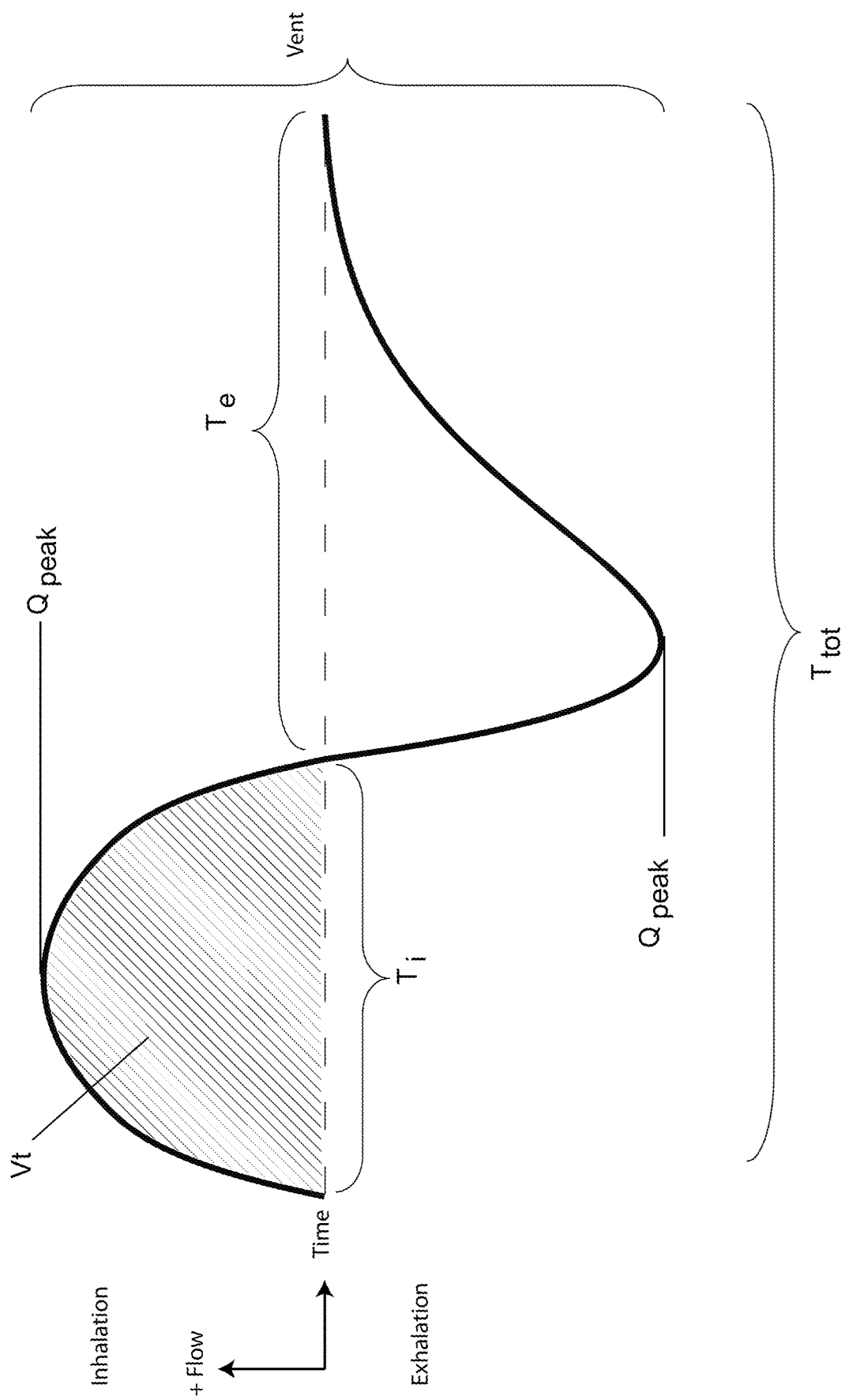

FIG. 4 shows a model typical breath waveform of a person while sleeping.

4.5 RPT Device and Humidifier

Figure 5A:
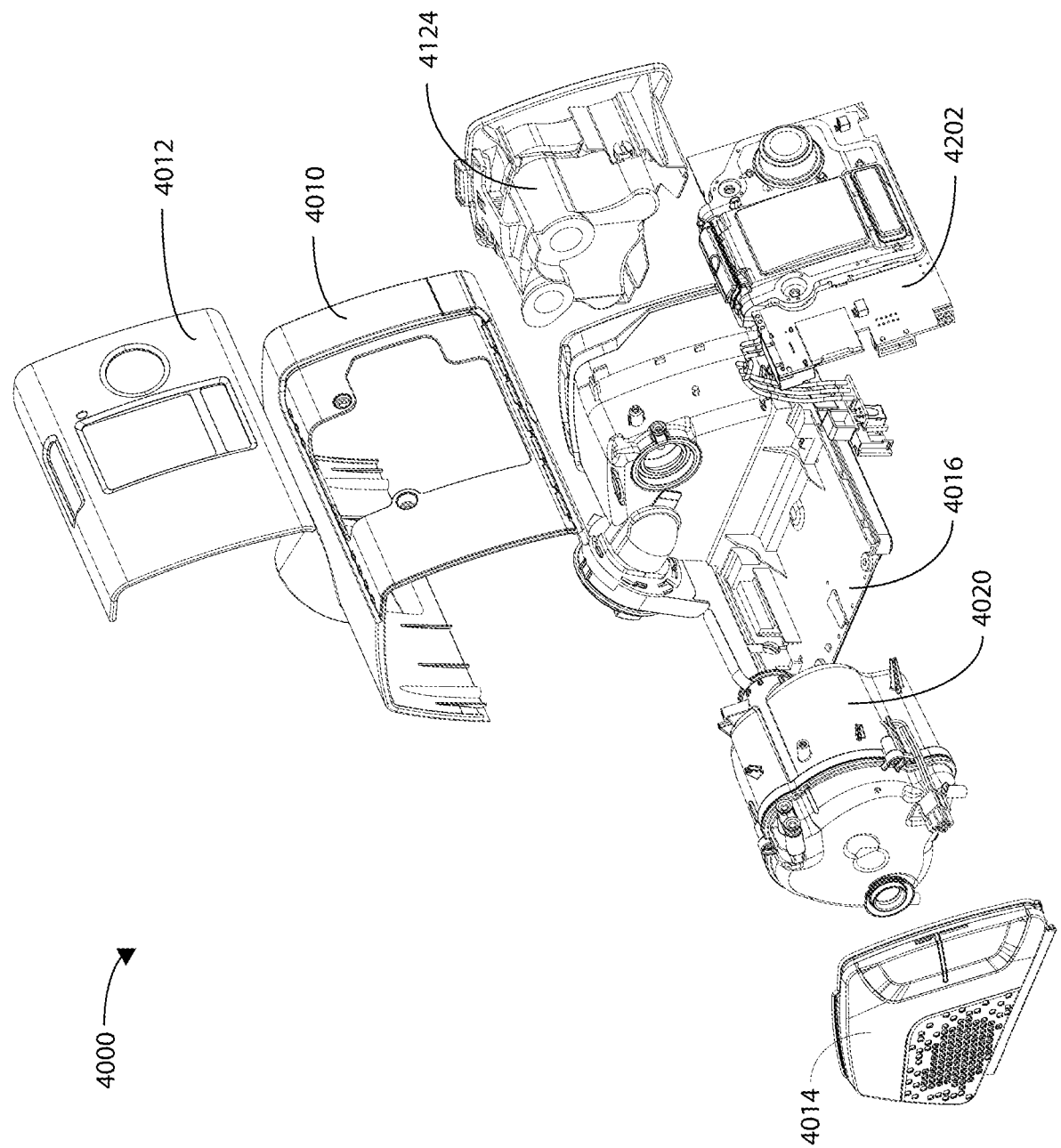

FIG. 5A shows an exploded perspective view of an RPT device 4000 in accordance with one form of the present technology.

Figure 5B:
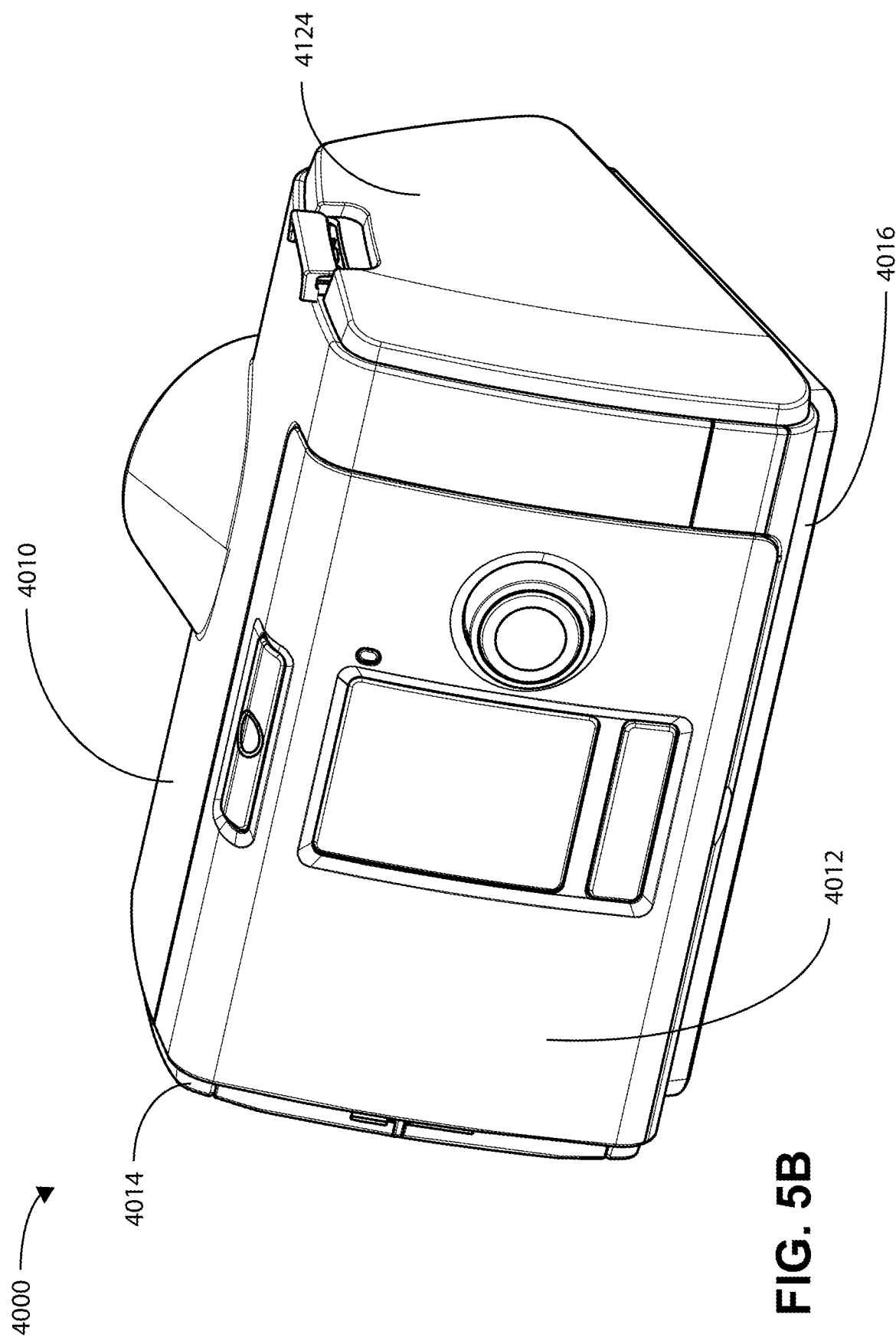

FIG. 5B shows a perspective view of an RPT device 4000 comprising an outlet cap with a muffler 4124 in accordance with one form of the present technology.

Figure 5C:
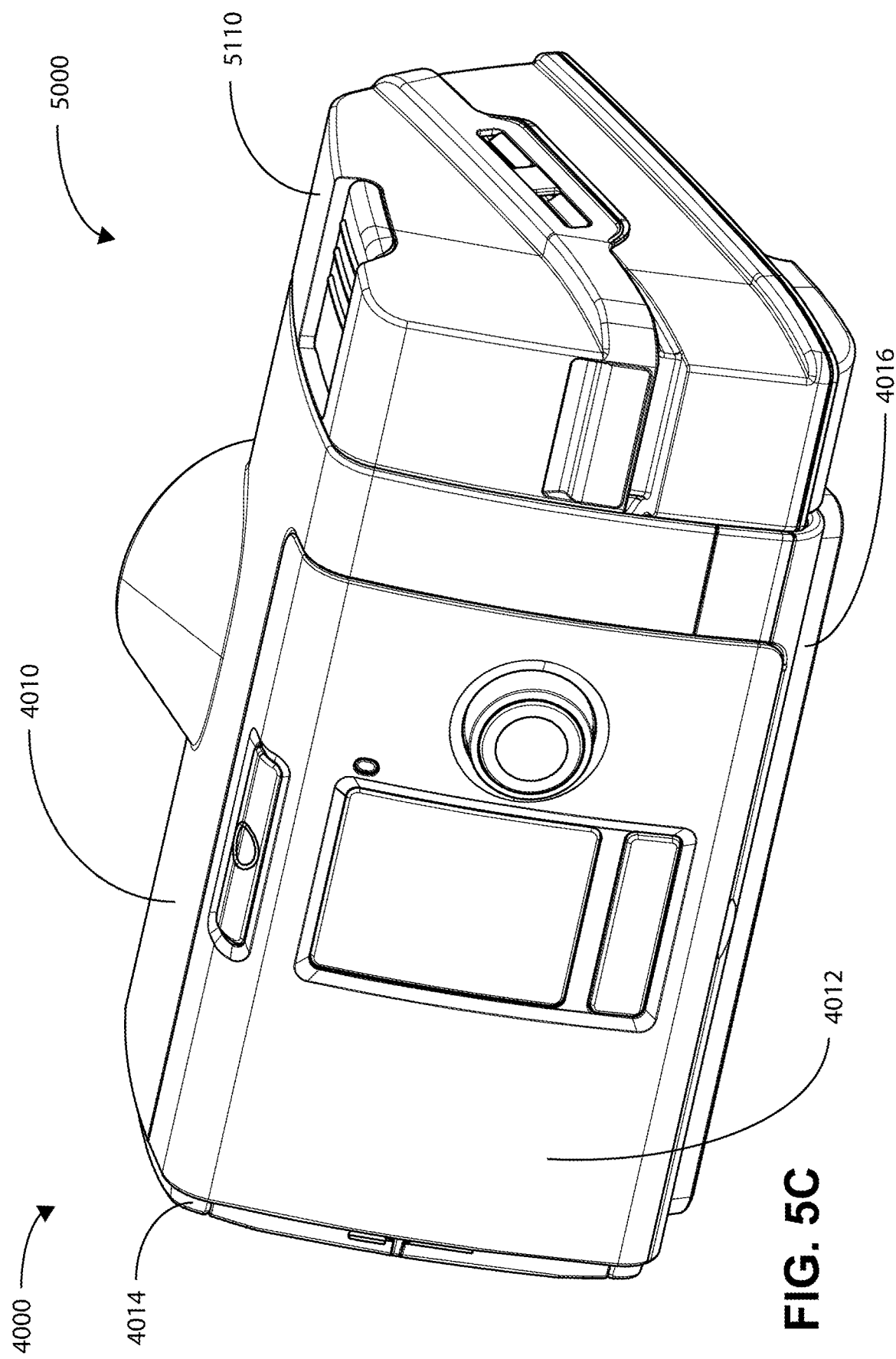

FIG. 5C shows a perspective view of an RPT device 4000 with an integrated humidifier 5000 comprising a water reservoir 5110 in accordance with one form of the present technology.

Figure 5D:
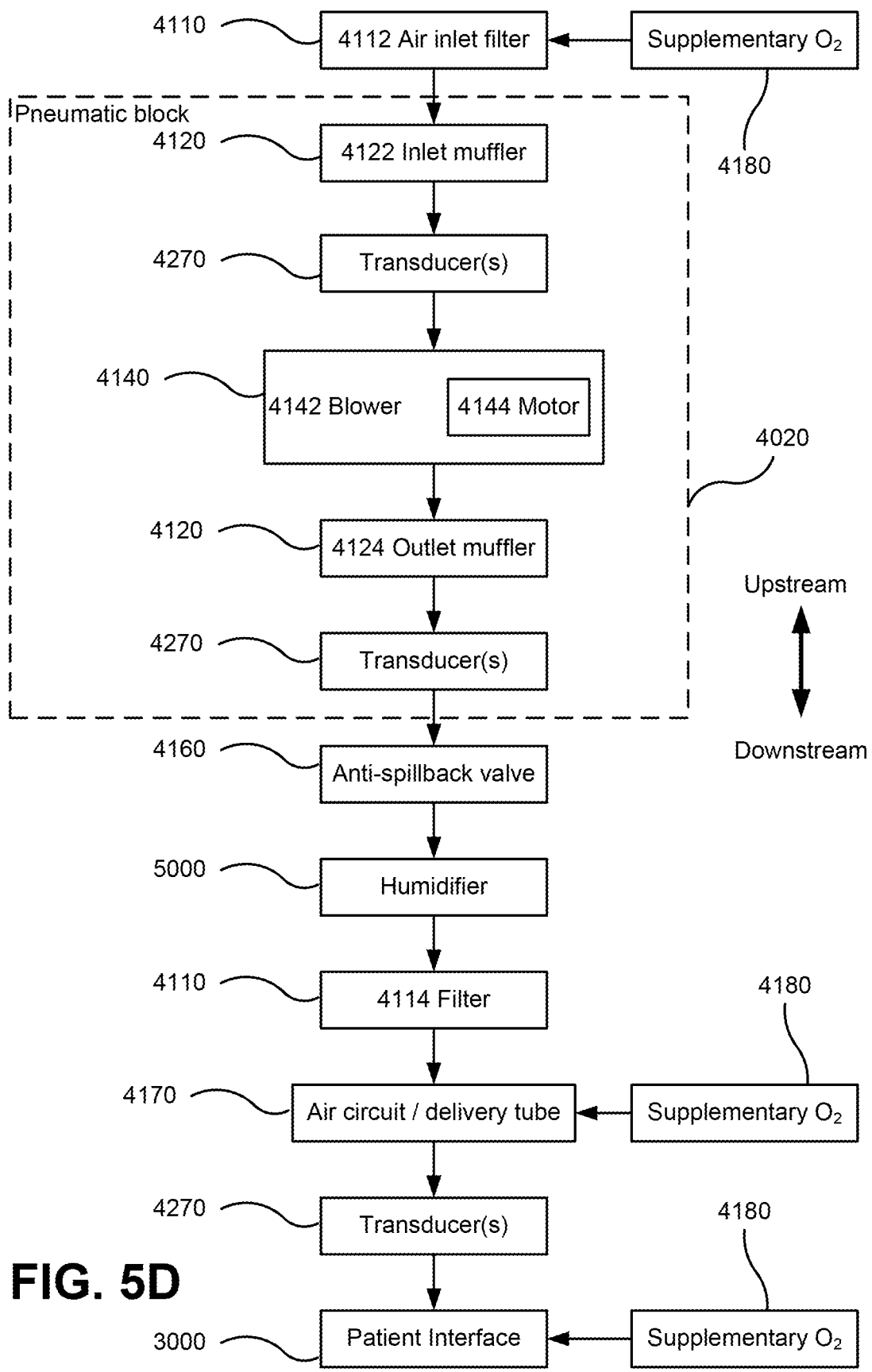

FIG. 5D is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

Figure 5E:
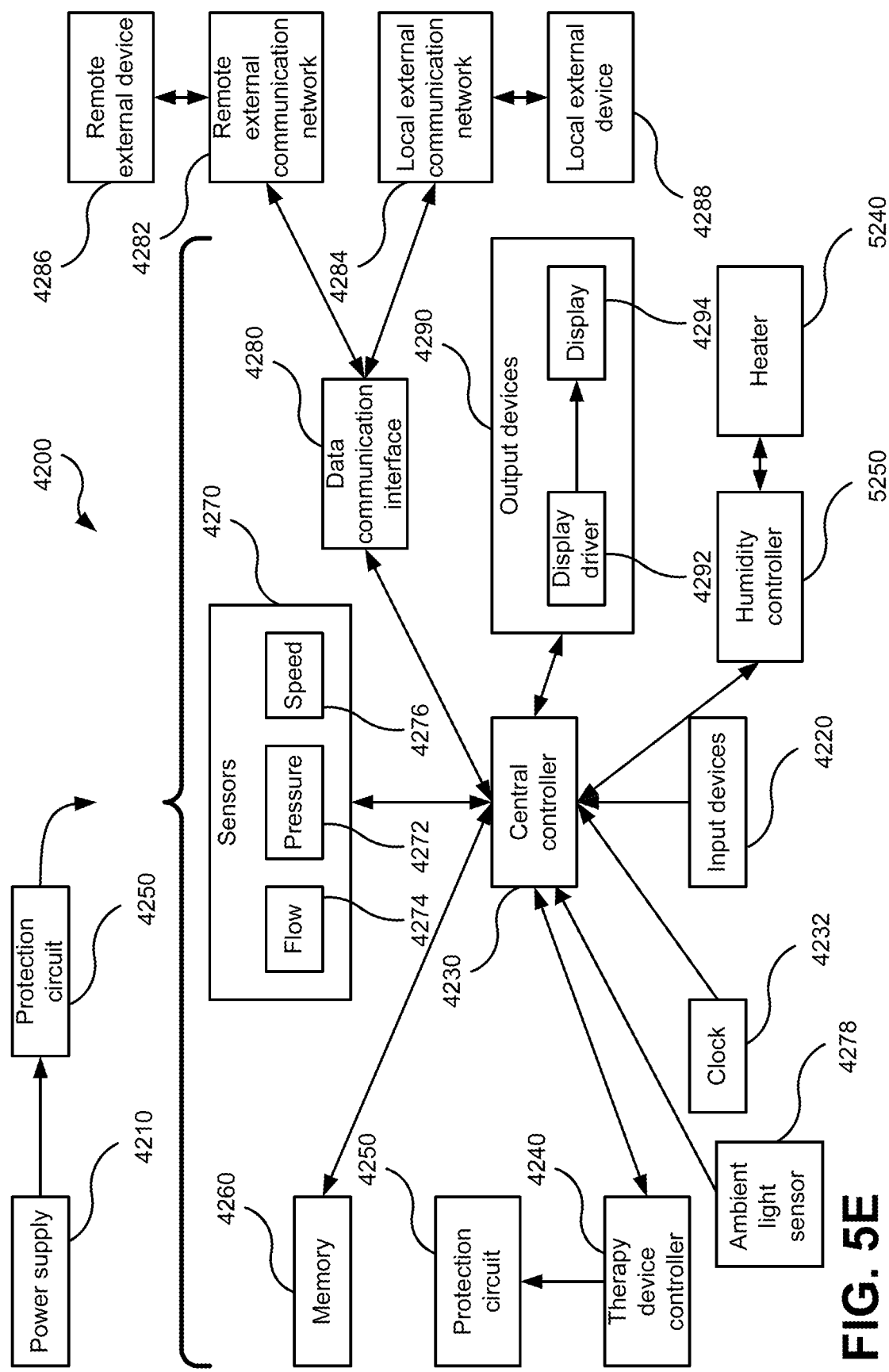

FIG. 5E is a schematic diagram of the electrical components of an RPT device in accordance with one form of the present technology.

Figure 5F:
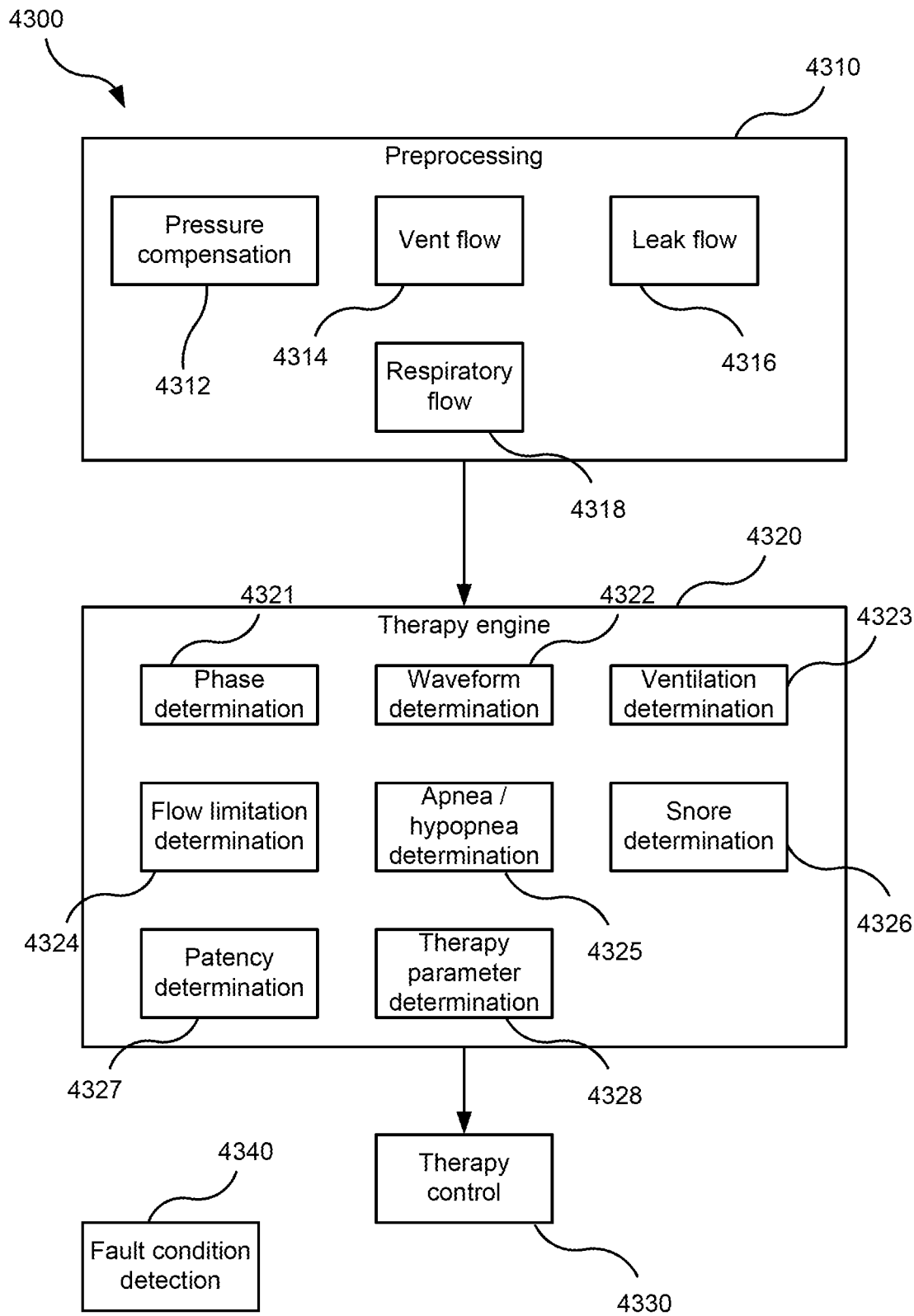

FIG. 5F is a schematic diagram of the algorithms implemented in an RPT device in accordance with one form of the present technology.

Figure 5G:
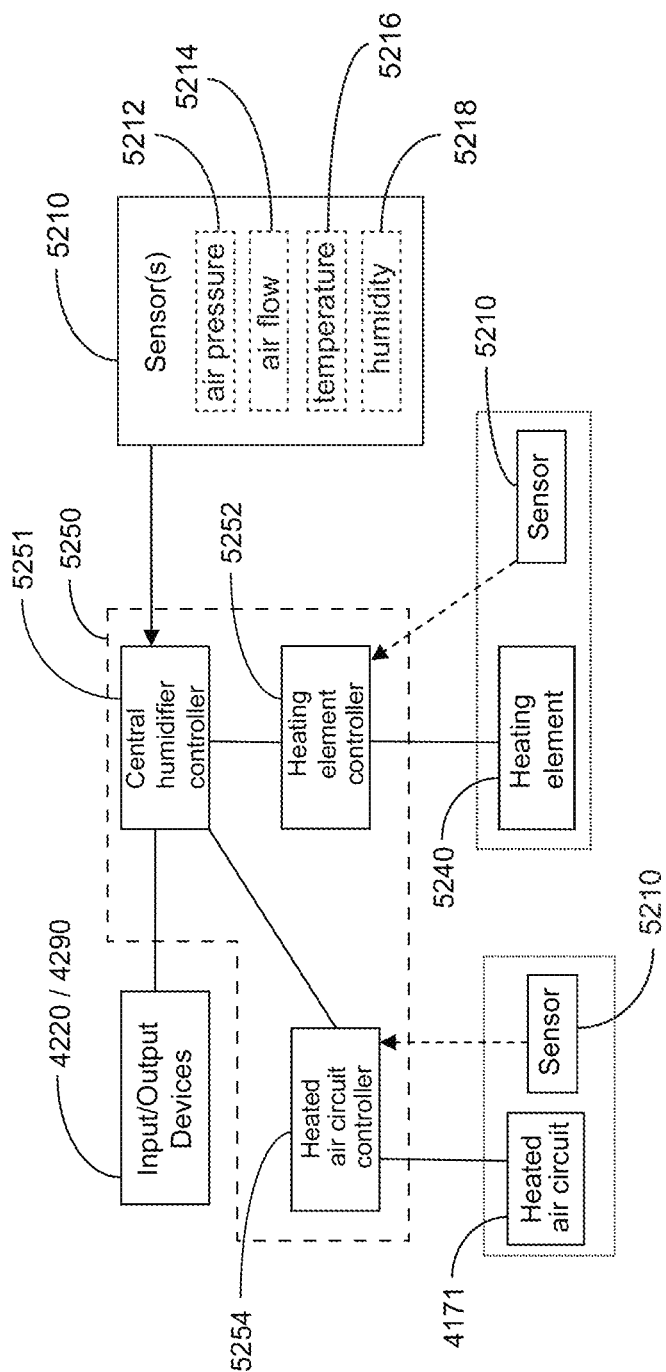

FIG. 5G shows a schematic of a humidifier in accordance with one form of the present technology.

Figure 6A:
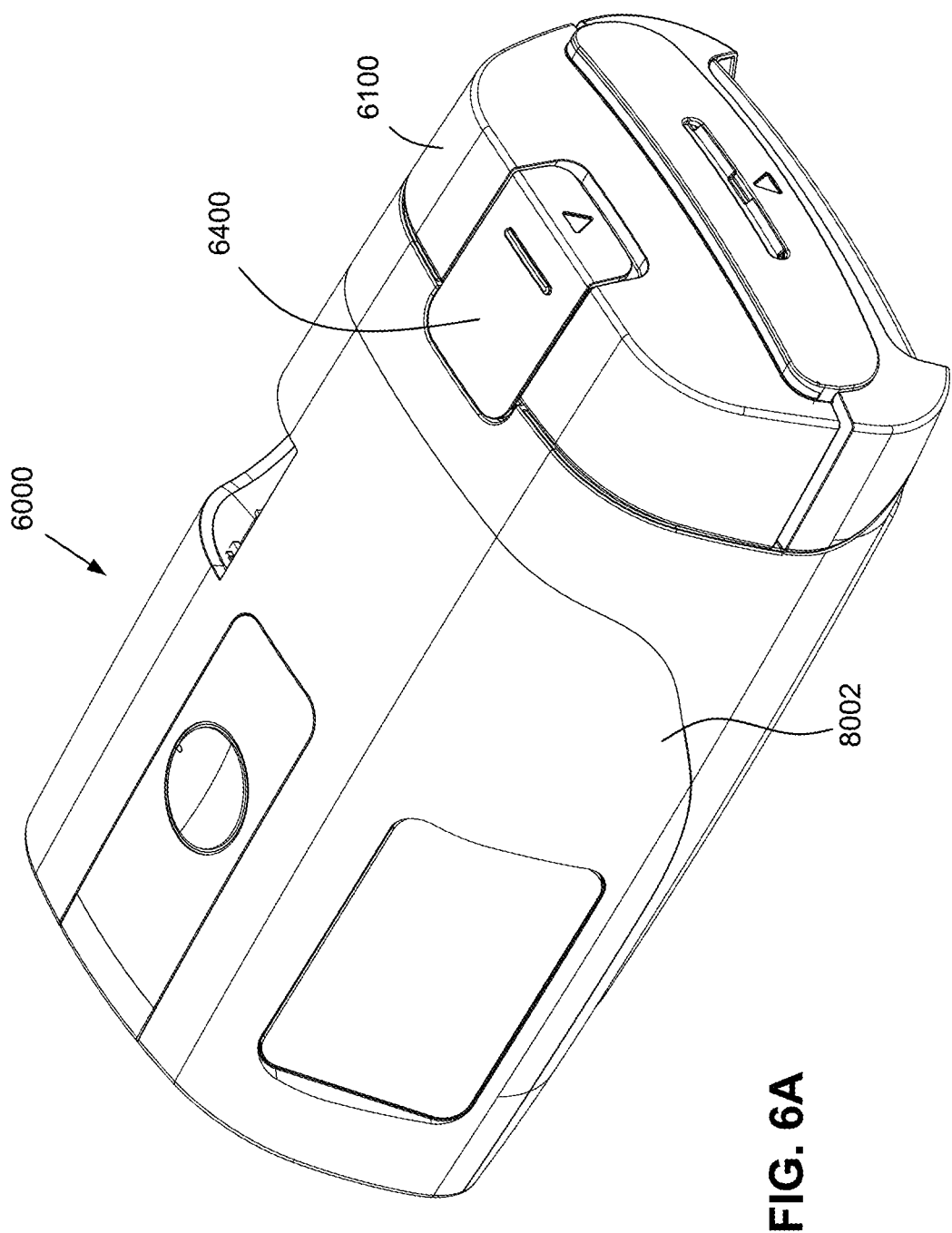

FIG. 6A is a perspective view of an integrated RPT device and humidifier comprising a water reservoir according to an example of the present technology.

Figure 6B:
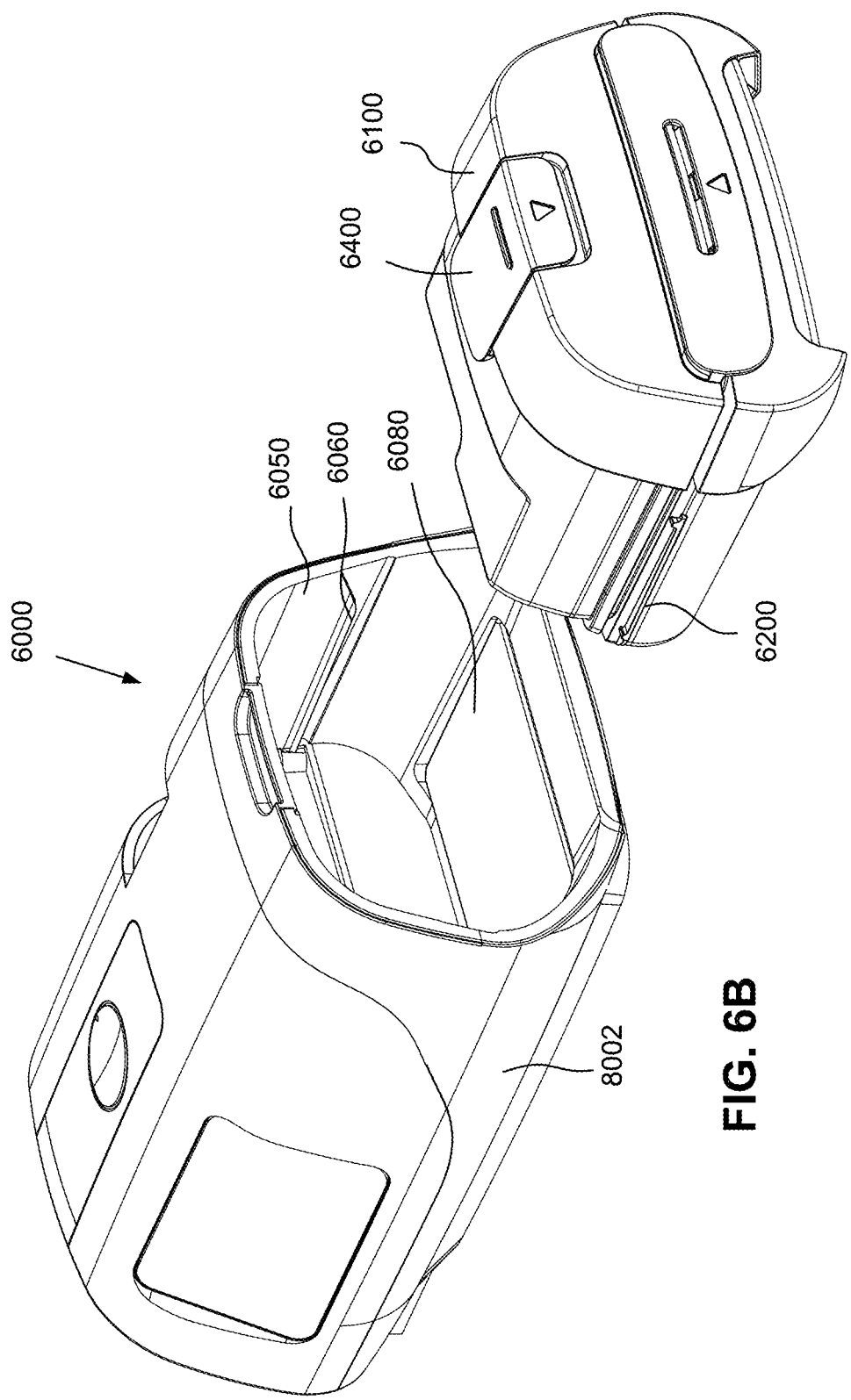

FIG. 6B is a perspective view of the integrated RPT device and humidifier of FIG. 6A with the water reservoir removed from the reservoir dock.

Figure 7:
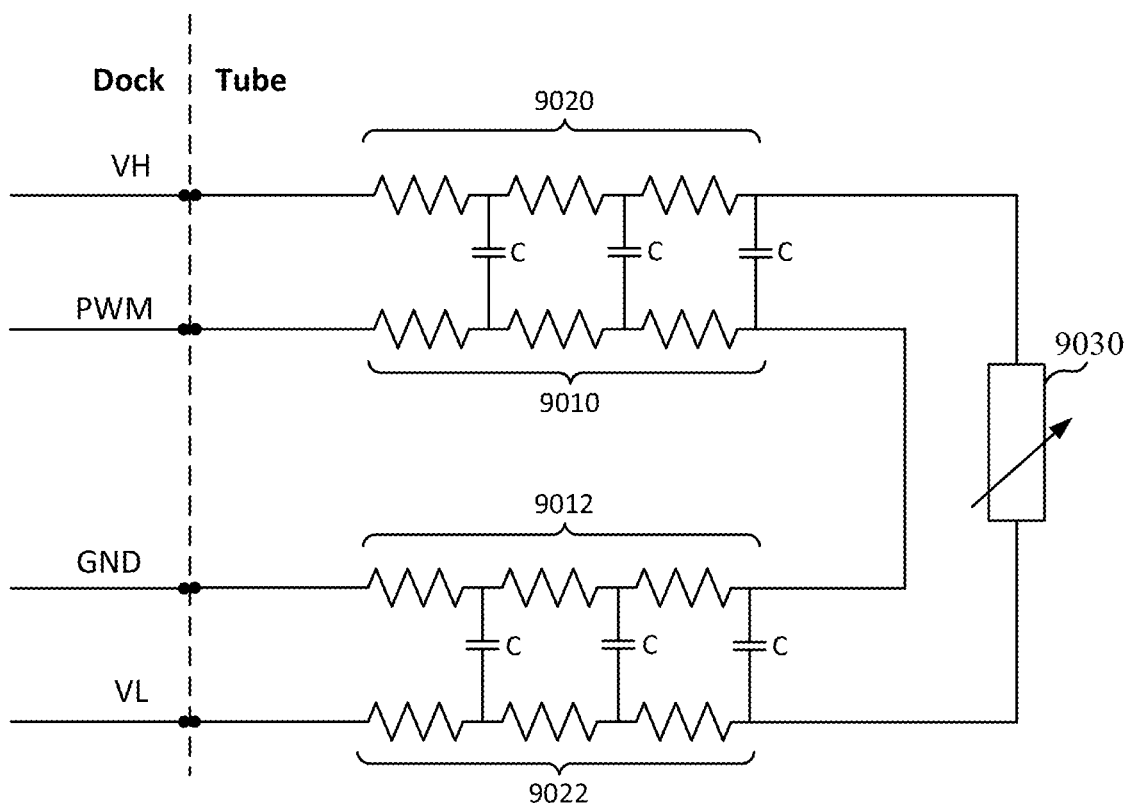

FIG. 7 shows a tube with a four wire circuit coupled to a dock in accordance with one form of the present technology.

Figure 8:
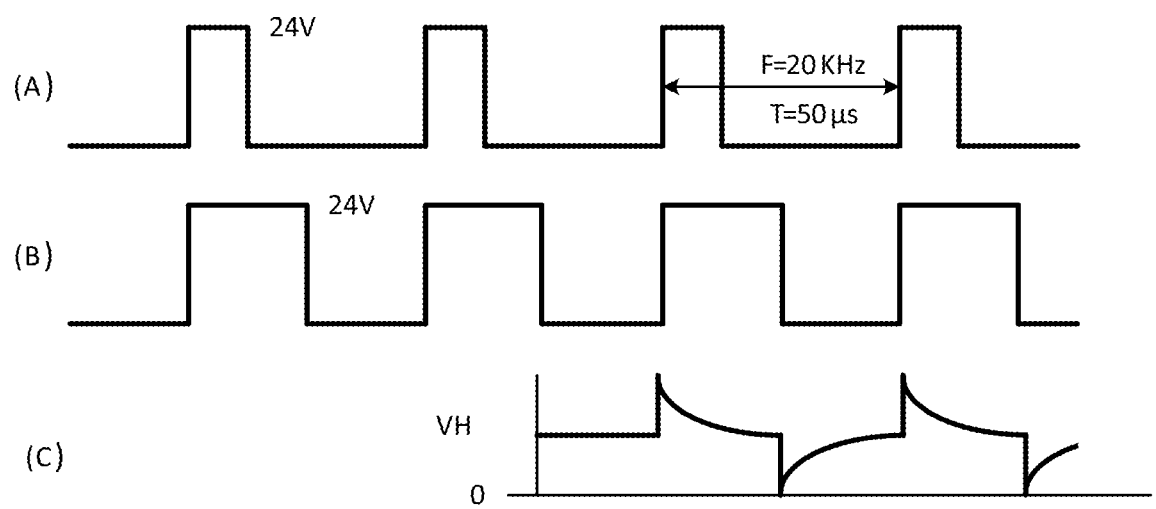

FIG. 8 shows an exemplary signal diagram of a PWM signal that may be applied to the heating elements and portions of PWM induced signal that may be observed in the sensing circuit.

Figure 9:
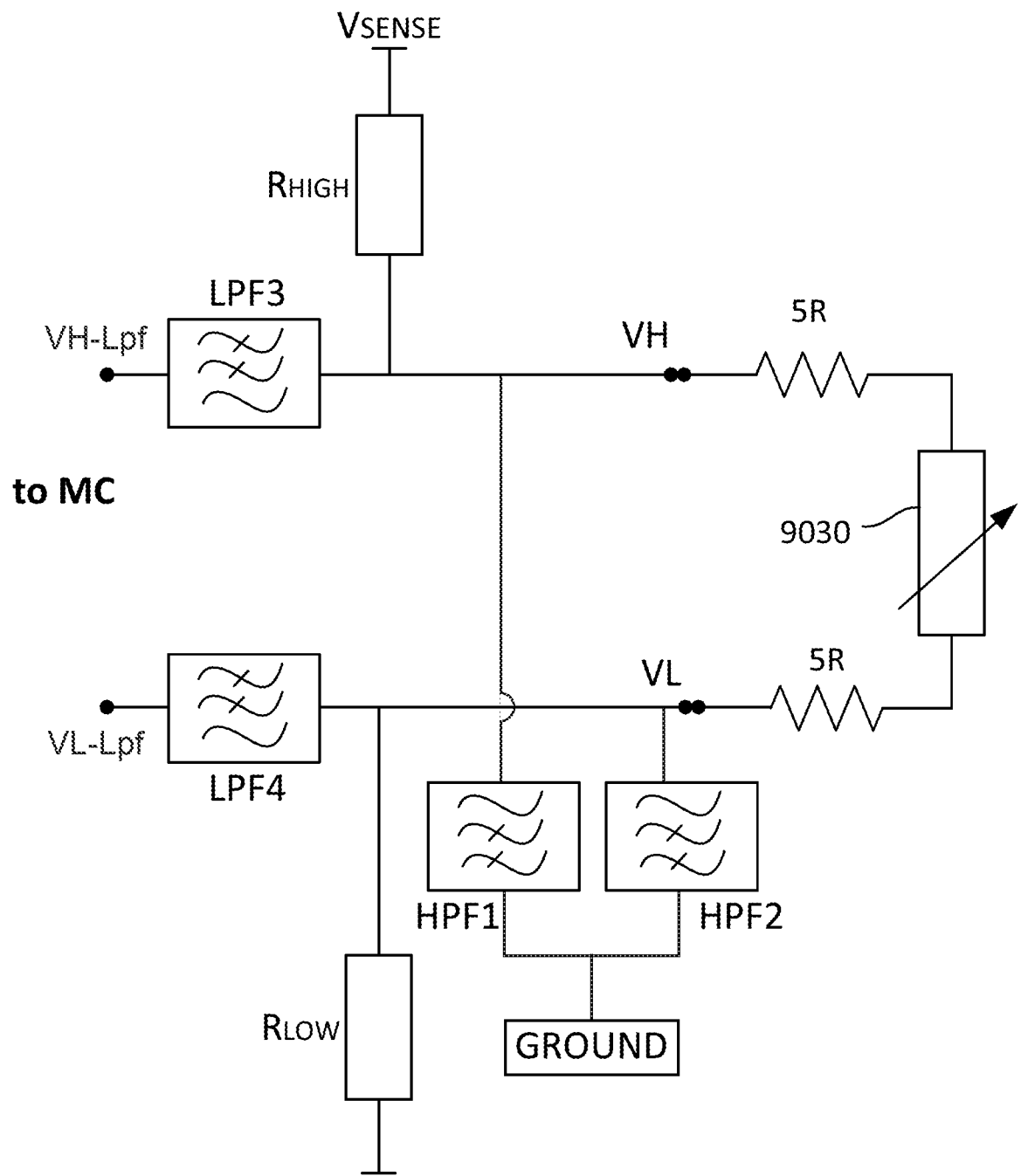

FIG. 9 shows an exemplary divider network including low pass filters in accordance with one form of the present technology.

Figure 10A:
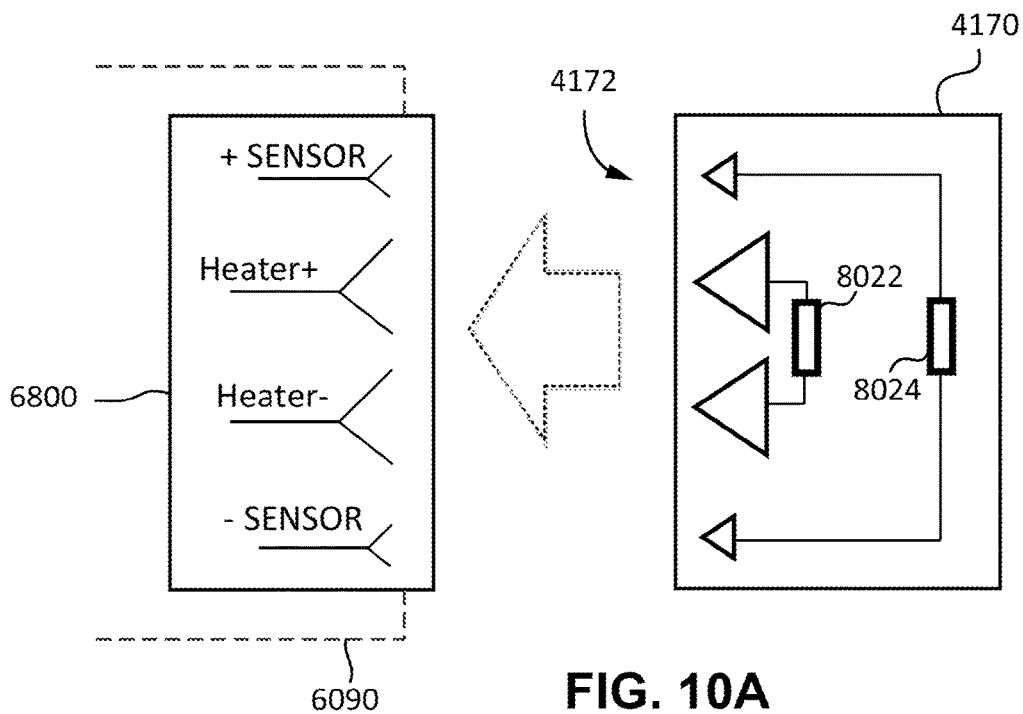
Figure 10B:
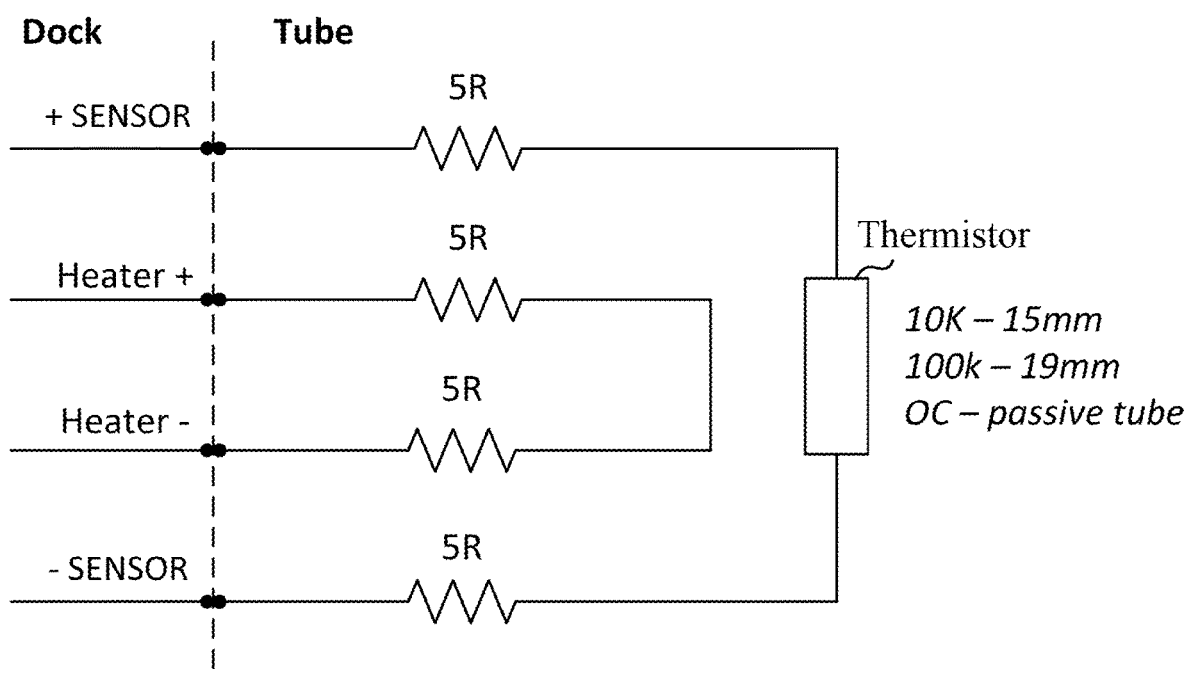

FIGS. 10A and 10B show a schematic electronic diagram of the dock and a tube connection in accordance with one form of the present technology.

FIG. 11 shows a dock and a tube schematic connection in accordance with another form of the present technology.

Figure 12:
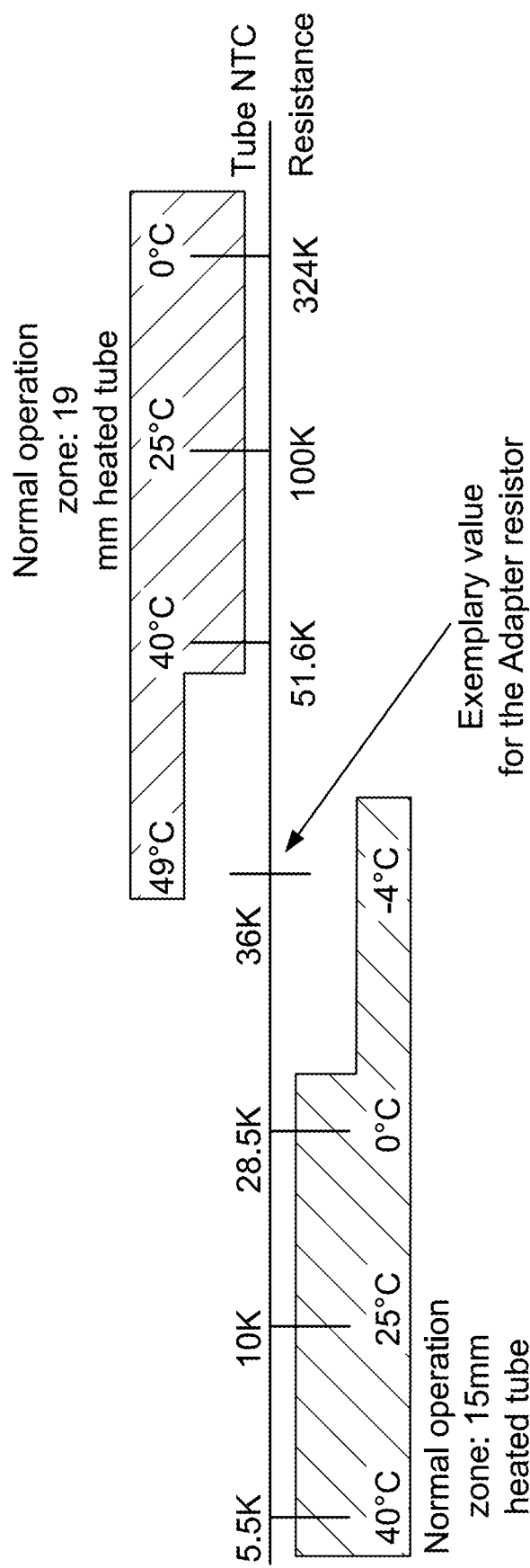

FIG. 12 shows exemplary tube NTC sensor resistance variations over different temperatures for a 100 k thermistor and a 10 k thermistor.

Figure 13:
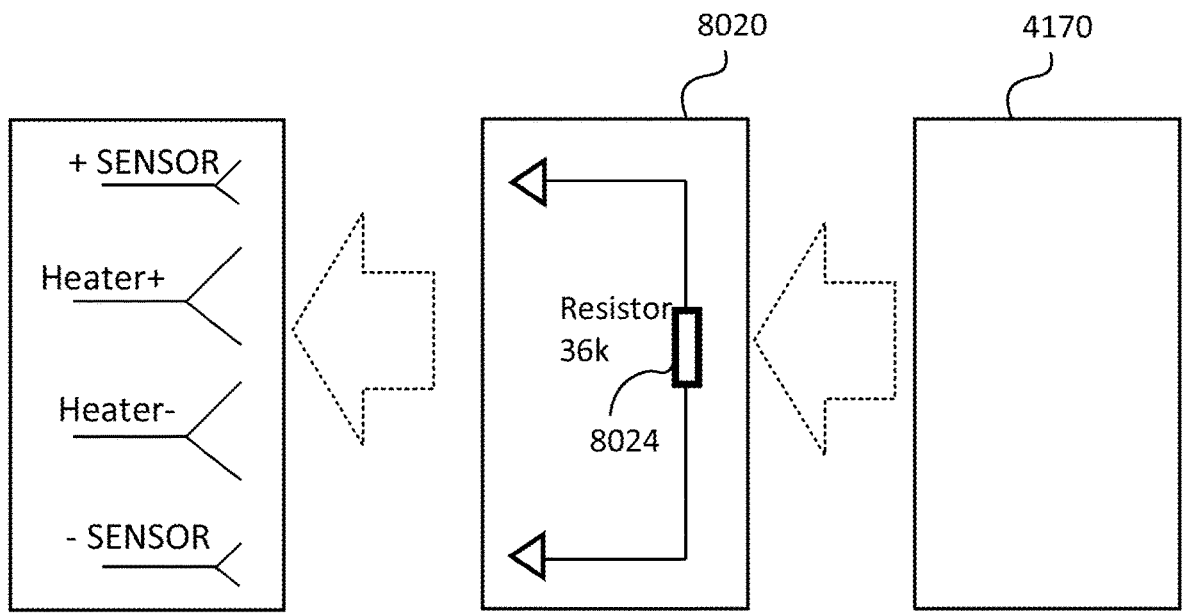

FIG. 13 shows a dock and a tube schematic connection in accordance with another form of the present technology.

Figure 14:
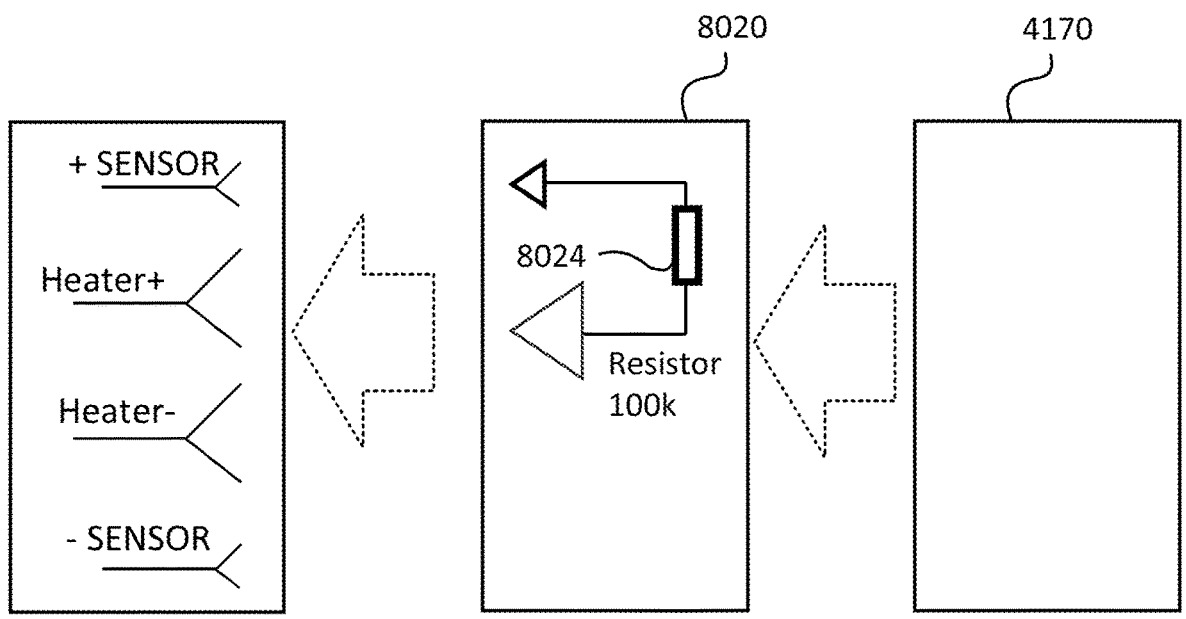

FIG. 14 shows a dock and a tube schematic connection in accordance with another form of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

Figure 1A:
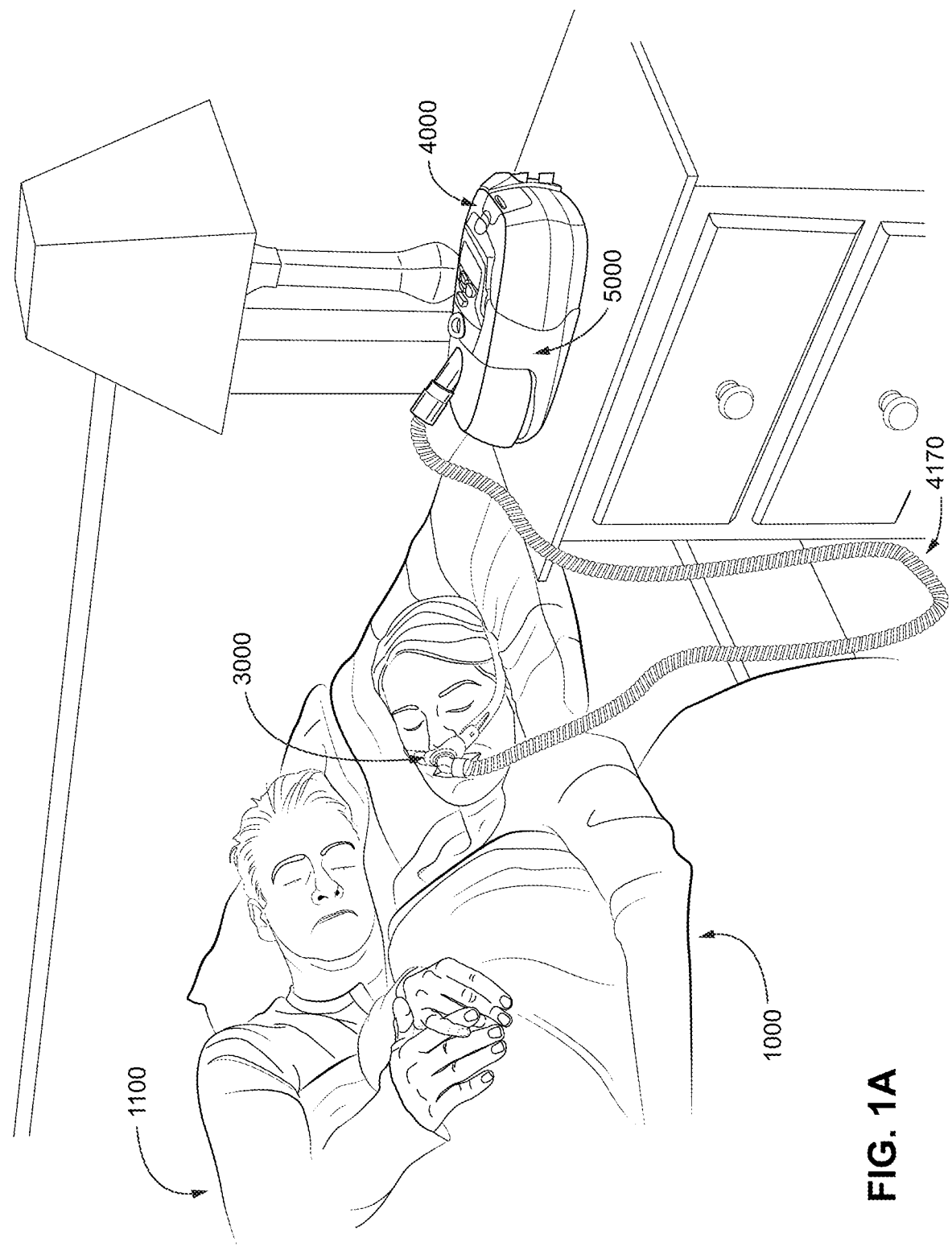
Figure 1B:
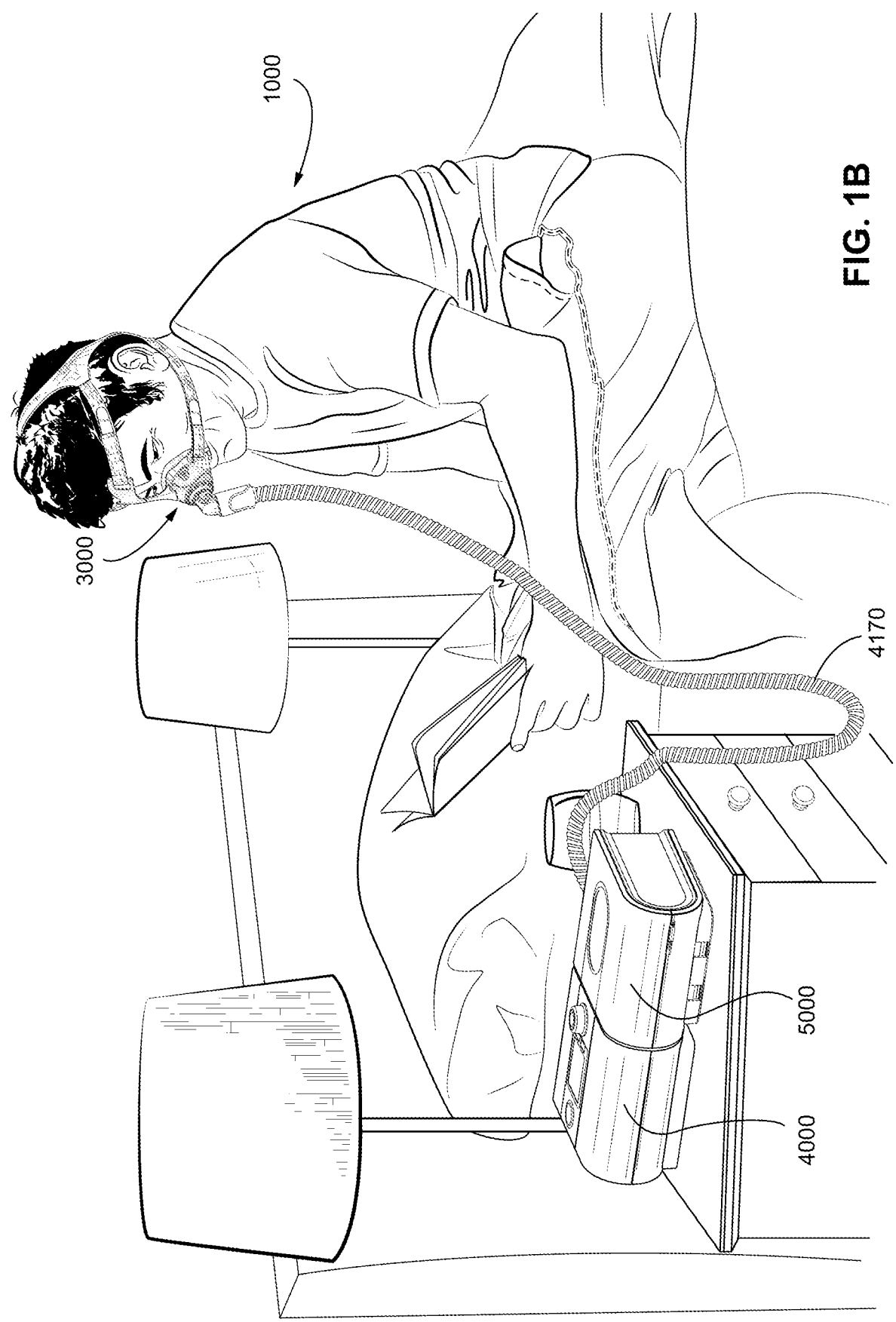
Figure 1C:
Figure 2A:
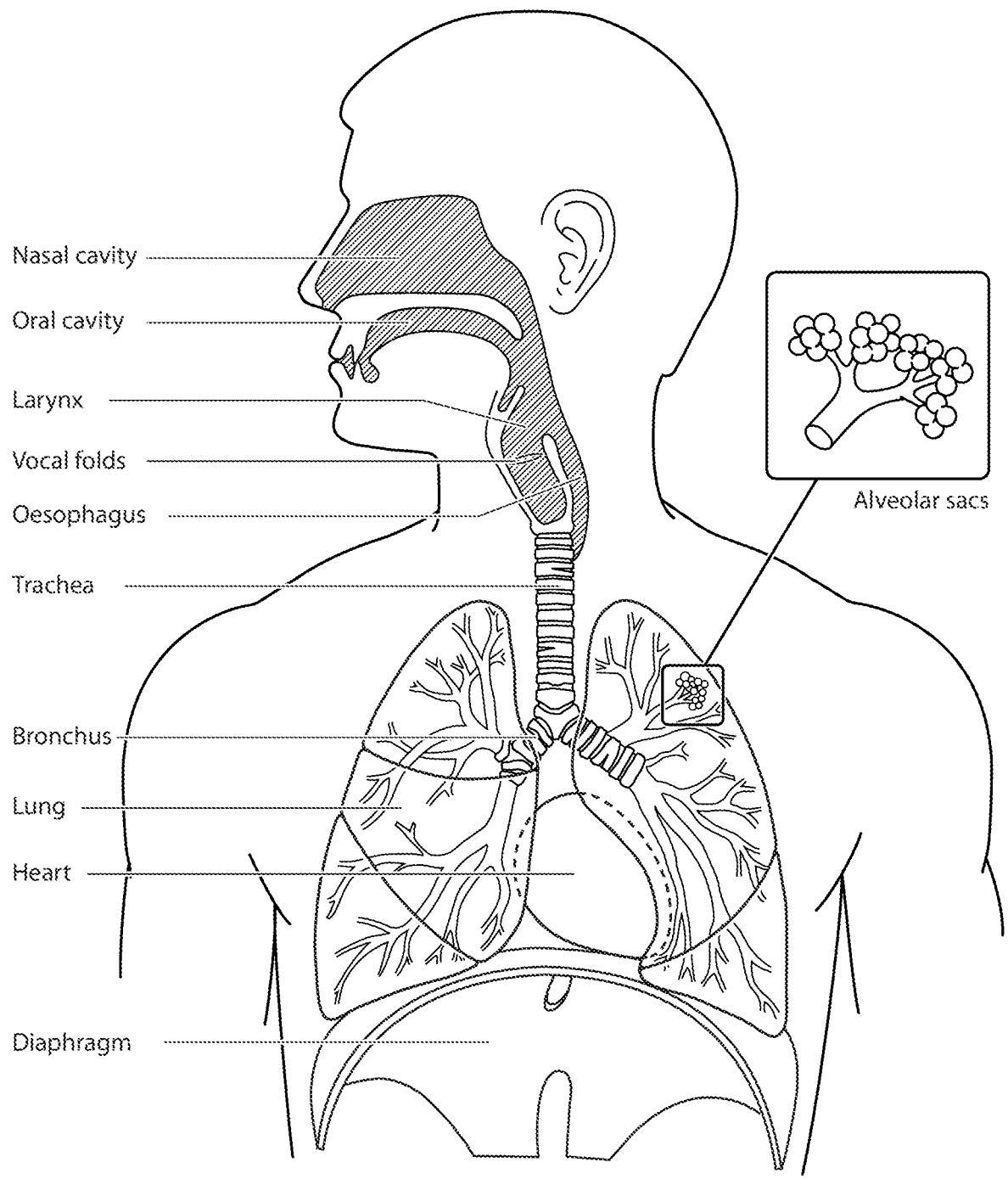
FIG. 2A shows an overview of a human respiratory system including the nasal and oral cavities, the larynx, vocal folds, oesophagus, trachea, bronchus, lung, alveolar sacs, heart and diaphragm.
Figure 2B:
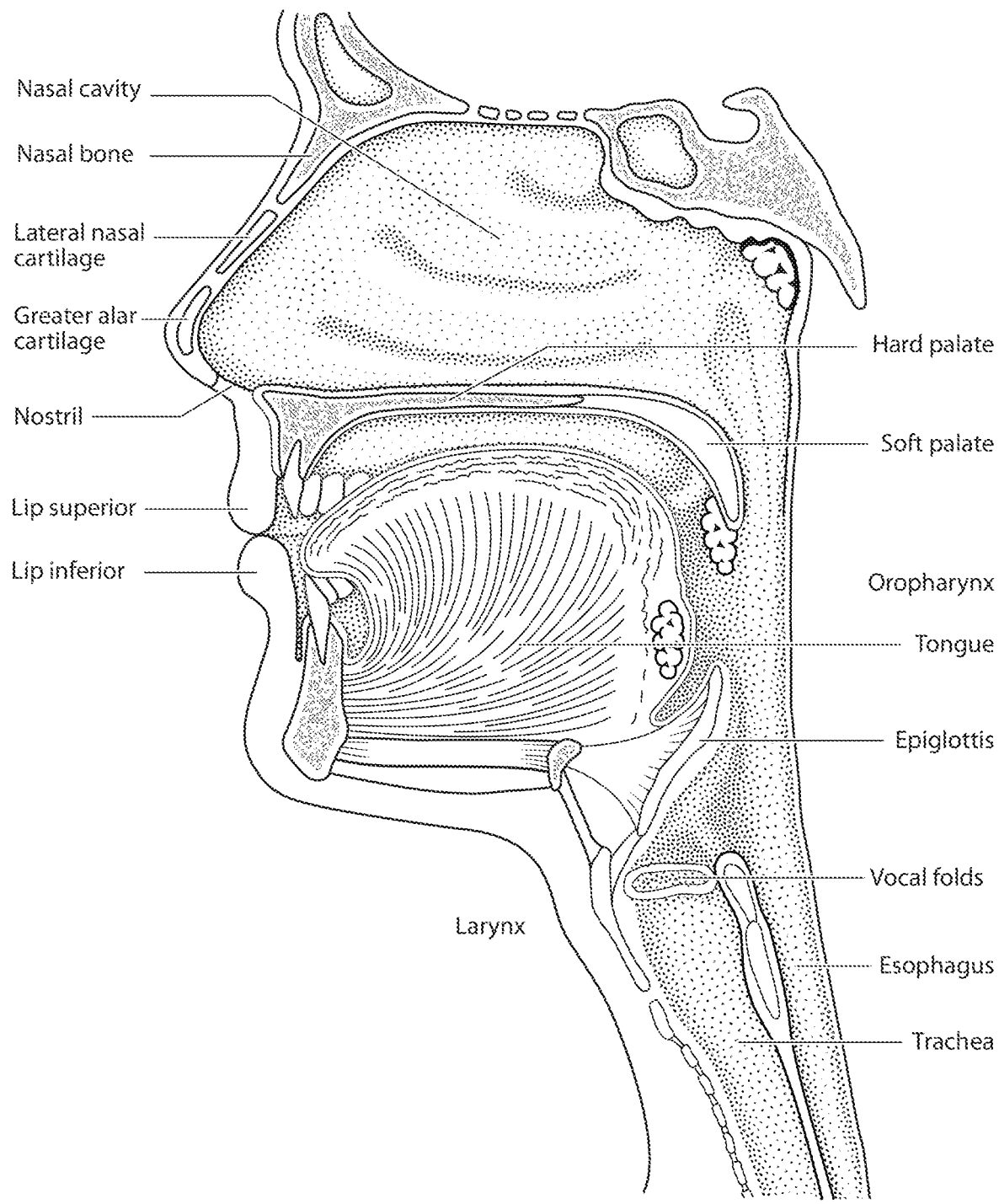
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

In one form, the present technology comprises an apparatus or device for treating a respiratory disorder. The apparatus or device may comprise an RPT device 4000 for supplying pressurised air to the patient 1000 via an air circuit 4170 to a patient interface 3000, e.g., see FIGS. 1A to 1C.

5.3 Patient Interface

FIG. 3 shows a non-invasive patient interface 3000 in accordance with one aspect of the present technology comprising the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.4 Rpt Device

An exploded view of an RPT device 4000 in accordance with one aspect of the present technology is shown in FIG. 5A. An RPT device 4000 may comprise mechanical, pneumatic, and/or electrical components and be configured to execute one or more algorithms. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10 cmH$_2$O, or at least 20 cmH$_2$O.

The RPT device 4000 may include an external housing having one or more panel(s) such as a main panel 4010, a front panel 4012 and a side panel 4014. The RPT device 4000 may also comprise an outlet cap with a muffler 4124 as shown in FIGS. 5A and 5B. The outlet cap with a muffler 4124 may be removable and replaced with a water reservoir 5110 (see FIG. 5C). In such forms, the RPT device 4000 may be considered to include an integrated humidifier 5000. Thus, the RPT device 4000 may be used with or without humidification depending upon whether the water reservoir 5110 or the outlet cap with a muffler 4124 respectively is attached. Preferably the RPT device 4000 comprises a chassis 4016 that supports one or more internal components of the RPT device 4000. In one form the RPT device 4000 comprises a pressure generator 4140, which may be housed in a pneumatic block 4020 coupled to the chassis 4016.

Further examples and details of an exemplary RPT device are described in PCT Publication No. WO 2015/089582, which is incorporated herein by reference in its entirety.

The pneumatic path of the RPT device 4000 (e.g. shown in FIG. 5D) may comprise an inlet air filter 4112, an inlet muffler 4122, a pressure generator 4140 capable of supplying air at positive pressure (preferably a blower 4142) and an outlet muffler 4124 (or a water reservoir 5110 if humidification is required). One or more transducers 4270, such as pressure sensors and flow sensors may be included in the pneumatic path. The pneumatic path may also include anti-spill back valve 4160 to prevent water from the humidifier 5000 spilling back to the electrical components of the RPT device 4000.

As shown in FIG. 5E, the RPT device 4000 may have an electrical power supply 4210, one or more input devices 4220, a central controller 4230, a therapy device controller 4240, one or more protection circuits 4250, memory 4260, sensors/transducers 4270, data communication interface 4280 and one or more output devices 4290. Electrical components 4200 may be mounted on a single Printed Circuit Board Assembly (PCBA) 4202 (e.g., see FIG. 5A). In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.4.1 Flow Rate Sensor

A flow rate sensor 4274 in accordance with the present technology may be based on a differential pressure transducer, for example, an SDP600 Series differential pressure transducer from SENSIRION.

In one form, a signal representing a flow rate from the flow rate sensor 4274 is received by the central controller 4230.

5.4.1.4.2 Pressure Sensor

A pressure sensor 4272 in accordance with the present technology is located in fluid communication with the pneumatic path. An example of a suitable pressure sensor is a transducer from the HONEYWELL ASDX series. An alternative suitable pressure sensor is a transducer from the NPA Series from GENERAL ELECTRIC.

In one form, a signal from the pressure sensor 4272 is received by the central controller 4230.

5.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 may be provided to the therapy device controller 4240. The motor speed transducer 4276 may, for example, be a speed sensor, such as a Hall effect sensor.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.2 RPT Device Electrical Components 5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form, the input device 4220 may be constructed and arranged to allow a person to select a value and/or a menu option.

5.4.2.3 Central Controller

In one form of the present technology, the central controller 4230 is one or a plurality of processors suitable to control an RPT device 4000.

Suitable processors may include an x86 INTEL processor, a processor based on ARM® Cortex®-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, one or more input devices 4220, and the humidifier 5000.

The central controller 4230 may be configured to provide output signal(s) to one or more of an output device 4290, a therapy device controller 4240, a data communication interface 4280, and the humidifier 5000.

In some forms of the present technology, the central controller 4230 is configured to implement the one or more methodologies described herein, such as the one or more algorithms 4300 expressed as computer programs stored in a non-transitory computer readable storage medium, such as memory 4260. In some forms of the present technology, the central controller 4230 may be integrated with an RPT device 4000. However, in some forms of the present technology, some methodologies may be performed by a remotely located device. For example, the remotely located device may determine control settings for a ventilator or detect respiratory related events by analysis of stored data such as from any of the sensors described herein.

5.4.2.4 Clock

The RPT device 4000 may include a clock 4232 that is connected to the central controller 4230.

5.4.2.5 Therapy Device Controller

In one form of the present technology, therapy device controller 4240 is a therapy control module 4330 that forms part of the algorithms 4300 executed by the central controller 4230.

In one form of the present technology, therapy device controller 4240 is a dedicated motor control integrated circuit. For example, in one form a MC33035 brushless DC motor controller, manufactured by ONSEMI is used.

5.4.2.6 Protection Circuits

The one or more protection circuits 4250 in accordance with the present technology may comprise an electrical protection circuit, a temperature and/or pressure safety circuit.

5.4.2.7 Memory

In accordance with one form of the present technology the RPT device 4000 includes memory 4260, e.g., non-volatile memory. In some forms, memory 4260 may include battery powered static RAM. In some forms, memory 4260 may include volatile RAM.

Memory 4260 may be located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms 4300.

5.4.2.8 Data Communication Systems

In one form of the present technology, a data communication interface 4280 is provided, and is connected to the central controller 4230. Data communication interface 4280 may be connectable to a remote external communication network 4282 and/or a local external communication network 4284. The remote external communication network 4282 may be connectable to a remote external device 4286. The local external communication network 4284 may be connectable to a local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, or a consumer infrared protocol.

In one form, remote external device 4286 is one or more computers, for example a cluster of networked computers. In one form, remote external device 4286 may be virtual computers, rather than physical computers. In either case, such a remote external device 4286 may be accessible to an appropriately authorised person such as a clinician.

The local external device 4288 may be a personal computer, mobile phone, tablet or remote control.

5.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

5.4.2.9.1 Display Driver

A display driver 4292 receives as an input the characters, symbols, or images intended for display on the display 4294, and converts them to commands that cause the display 4294 to display those characters, symbols, or images.

5.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.4.3 RPT Device Algorithms

As mentioned above, in some forms of the present technology, the central controller 4230 may be configured to implement one or more algorithms 4300 expressed as computer programs stored in a non-transitory computer readable storage medium, such as memory 4260. The algorithms 4300 are generally grouped into groups referred to as modules, e.g., see FIG. 5F.

5.4.3.1 Pre-Processing Module

A pre-processing module 4310 in accordance with one form of the present technology receives as an input a signal from a transducer 4270, for example a flow rate sensor 4274 or pressure sensor 4272, and performs one or more process steps to calculate one or more output values that will be used as an input to another module, for example a therapy engine module 4320.

In one form of the present technology, the output values include the interface or mask pressure Pm, the respiratory flow rate Qr, and the leak flow rate Ql.

In various forms of the present technology, the pre-processing module 4310 comprises one or more of the following algorithms: pressure compensation 4312, vent flow rate estimation 4314, leak flow rate estimation 4316, and respiratory flow rate estimation 4318.

5.4.3.1.1 Pressure Compensation

In one form of the present technology, a pressure compensation algorithm 4312 receives as an input a signal indicative of the pressure in the pneumatic path proximal to an outlet of the pneumatic block. The pressure compensation algorithm 4312 estimates the pressure drop through the air circuit 4170 and provides as an output an estimated pressure, Pm, in the patient interface 3000.

5.4.3.1.2 Vent flow Rate Estimation

In one form of the present technology, a vent flow rate estimation algorithm 4314 receives as an input an estimated pressure, Pm, in the patient interface 3000 and estimates a vent flow rate of air, Qv, from a vent 3400 in a patient interface 3000.

5.4.3.1.3 Leak Flow Rate Estimation

In one form of the present technology, a leak flow rate estimation algorithm 4316 receives as an input a total flow rate, Qt, and a vent flow rate Qv, and provides as an output an estimate of the leak flow rate Ql. In one form, the leak flow rate estimation algorithm estimates the leak flow rate Ql by calculating an average of the difference between total flow rate Qt and vent flow rate Qv over a period sufficiently long to include several breathing cycles, e.g. about 10 seconds.

In one form, the leak flow rate estimation algorithm 4316 receives as an input a total flow rate Qt, a vent flow rate Qv, and an estimated pressure, Pm, in the patient interface 3000, and provides as an output a leak flow rate Ql, by calculating a leak conductance, and determining a leak flow rate Ql to be a function of leak conductance and pressure, Pm. Leak conductance is calculated as the quotient of low pass filtered non-vent flow rate equal to the difference between total flow rate Qt and vent flow rate Qv, and low pass filtered square root of pressure Pm, where the low pass filter time constant has a value sufficiently long to include several breathing cycles, e.g. about 10 seconds. The leak flow rate Ql may be estimated as the product of leak conductance and a function of pressure, Pm.

5.4.3.1.4 Respiratory Flow Rate Estimation

In one form of the present technology, a respiratory flow rate estimation algorithm 4318 receives as an input a total flow rate, Qt, a vent flow rate, Qv, and a leak flow rate, Ql, and estimates a respiratory flow rate of air, Qr, to the patient, by subtracting the vent flow rate Qv and the leak flow rate Ql from the total flow rate Qt.

5.4.3.2 Therapy Engine Module

In one form of the present technology, a therapy engine module 4320 receives as inputs one or more of a pressure, Pm, in a patient interface 3000, and a respiratory flow rate of air to a patient, Qr, and provides as an output one or more therapy parameters.

In one form of the present technology, a therapy parameter is a treatment pressure Pt.

In one form of the present technology, therapy parameters are one or more of an amplitude of a pressure variation, a base pressure, and a target ventilation.

In various forms, the therapy engine module 4320 comprises one or more of the following algorithms: phase determination 4321, waveform determination 4322, ventilation determination 4323, inspiratory flow limitation determination 4324, apnea/hypopnea determination 4325, snore determination 4326, airway patency determination 4327, target ventilation determination 4328, and therapy parameter determination 4329.

5.4.3.2.1 Phase Determination

In one form of the present technology, the RPT device 4000 does not determine phase.

In one form of the present technology, a phase determination algorithm 4321 receives as an input a signal indicative of respiratory flow rate, Qr, and provides as an output a phase Φ of a current breathing cycle of a patient 1000.

In some forms, known as discrete phase determination, the phase output Φ is a discrete variable. One implementation of discrete phase determination provides a bi-valued phase output Φ with values of either inhalation or exhalation, for example represented as values of 0 and 0.5 revolutions respectively, upon detecting the start of spontaneous inhalation and exhalation respectively. RPT devices 4000 that "trigger" and "cycle" effectively perform discrete phase determination, since the trigger and cycle points are the instants at which the phase changes from exhalation to inhalation and from inhalation to exhalation, respectively. In one implementation of bi-valued phase determination, the phase output Φ is determined to have a discrete value of 0 (thereby "triggering" the RPT device 4000) when the respiratory flow rate Qr has a value that exceeds a positive threshold, and a discrete value of 0.5 revolutions (thereby "cycling" the RPT device 4000) when a respiratory flow rate Qr has a value that is more negative than a negative threshold. The inhalation time Ti and the exhalation time Te may be estimated as typical values over many respiratory cycles of the time spent with phase Φ equal to 0 (indicating inspiration) and 0.5 (indicating expiration) respectively.

Another implementation of discrete phase determination provides a tri-valued phase output Φ with a value of one of inhalation, mid-inspiratory pause, and exhalation.

In other forms, known as continuous phase determination, the phase output Φ is a continuous variable, for example varying from 0 to 1 revolutions, or 0 to $2\pi$ radians. RPT devices 4000 that perform continuous phase determination may trigger and cycle when the continuous phase reaches 0 and 0.5 revolutions, respectively. In one implementation of continuous phase determination, a continuous value of phase Φ is determined using a fuzzy logic analysis of the respiratory flow rate Qr. A continuous value of phase determined in this implementation is often referred to as "fuzzy phase". In one implementation of a fuzzy phase determination algorithm 4321, the following rules are applied to the respiratory flow rate Qr:

1. If the respiratory flow rate is zero and increasing fast then the phase is 0 revolutions.
2. If the respiratory flow rate is large positive and steady then the phase is 0.25 revolutions.
3. If the respiratory flow rate is zero and falling fast, then the phase is 0.5 revolutions.
4. If the respiratory flow rate is large negative and steady then the phase is 0.75 revolutions.
5. If the respiratory flow rate is zero and steady and the 5-second low-pass filtered absolute value of the respiratory flow rate is large then the phase is 0.9 revolutions.
6. If the respiratory flow rate is positive and the phase is expiratory, then the phase is 0 revolutions.
7. If the respiratory flow rate is negative and the phase is inspiratory, then the phase is 0.5 revolutions.
8. If the 5-second low-pass filtered absolute value of the respiratory flow rate is large, the phase is increasing at a steady rate equal to the patient's breathing rate, low-pass filtered with a time constant of 20 seconds.

The output of each rule may be represented as a vector whose phase is the result of the rule and whose magnitude is the fuzzy extent to which the rule is true. The fuzzy extent to which the respiratory flow rate is "large", "steady", etc. is determined with suitable membership functions. The results of the rules, represented as vectors, are then combined by some function such as taking the centroid. In such a combination, the rules may be equally weighted, or differently weighted.

In another implementation of continuous phase determination, the phase Φ is first discretely estimated from the respiratory flow rate Qr as described above, as are the inhalation time Ti and the exhalation time Te. The continuous phase Φ at any instant may be determined as the half the proportion of the inhalation time Ti that has elapsed since the previous trigger instant, or 0.5 revolutions plus half the proportion of the exhalation time Te that has elapsed since the previous cycle instant (whichever instant was more recent).

5.4.3.2.2 Waveform Determination

In one form of the present technology, the therapy parameter determination algorithm 4329 provides an approximately constant treatment pressure throughout a respiratory cycle of a patient.

In other forms of the present technology, the therapy control module 4330 controls the pressure generator 4140 to provide a treatment pressure Pt that varies as a function of phase Φ of a respiratory cycle of a patient according to a waveform template Πp).

In one form of the present technology, a waveform determination algorithm 4322 provides a waveform template Π(Φ) with values in the range [0, 1] on the domain of phase values Φ provided by the phase determination algorithm 4321 to be used by the therapy parameter determination algorithm 4329.

In one form, suitable for either discrete or continuously-valued phase, the waveform template Π(Φ) is a square-wave template, having a value of 1 for values of phase up to and including 0.5 revolutions, and a value of 0 for values of phase above 0.5 revolutions. In one form, suitable for continuously-valued phase, the waveform template Π(Φ) comprises two smoothly curved portions, namely a smoothly curved (e.g. raised cosine) rise from 0 to 1 for values of phase up to 0.5 revolutions, and a smoothly curved (e.g. exponential) decay from 1 to 0 for values of phase above 0.5 revolutions. In one form, suitable for continuously-valued phase, the waveform template Π(Φ) is based on a square wave, but with a smooth rise from 0 to 1 for values of phase up to a "rise time" that is less than 0.5 revolutions, and a smooth fall from 1 to 0 for values of phase within a "fall time" after 0.5 revolutions, with a "fall time" that is less than 0.5 revolutions.

In some forms of the present technology, the waveform determination algorithm 4322 selects a waveform template Π(Φ) from a library of waveform templates, dependent on a setting of the RPT device. Each waveform template Π(Φ) in the library may be provided as a lookup table of values LI against phase values Φ. In other forms, the waveform determination algorithm 4322 computes a waveform template Π(Φ) "on the fly" using a predetermined functional form, possibly parametrised by one or more parameters (e.g. time constant of an exponentially curved portion). The parameters of the functional form may be predetermined or dependent on a current state of the patient 1000.

In some forms of the present technology, suitable for discrete bi-valued phase of either inhalation (Φ=0 revolutions) or exhalation (Φ=0.5 revolutions), the waveform determination algorithm 4322 computes a waveform template Π "on the fly" as a function of both discrete phase Φ and time t measured since the most recent trigger instant. In one such form, the waveform determination algorithm 4322 computes the waveform template Π(Φ, t) in two portions (inspiratory and expiratory) as follows:

$$\Pi(\Phi, t) = \begin{cases} \Pi_i(t), & \Phi = 0 \\ \Pi_e(t - T_i), & \Phi = 0.5 \end{cases}$$

where $\Pi_i(t)$ and $\Pi_e(t)$ are inspiratory and expiratory portions of the waveform template Π(Φ, t). In one such form, the inspiratory portion $\Pi_i(t)$ of the waveform template is a smooth rise from 0 to 1 parametrised by a rise time, and the expiratory portion $\Pi_e(t)$ of the waveform template is a smooth fall from 1 to 0 parametrised by a fall time.

5.4.3.2.3 Ventilation Determination

In one form of the present technology, a ventilation determination algorithm 4323 receives an input a respiratory flow rate Qr, and determines a measure indicative of current patient ventilation, Vent.

In some implementations, the ventilation determination algorithm 4323 determines a measure of ventilation Vent that is an estimate of actual patient ventilation. One such implementation is to take half the absolute value of respiratory flow rate, Qr, optionally filtered by low-pass filter such as a second order Bessel low-pass filter with a corner frequency of 0.11 Hz.

In other implementations, the ventilation determination algorithm 4323 determines a measure of ventilation Vent that is broadly proportional to actual patient ventilation. One such implementation estimates peak respiratory flow rate Qpeak over the inspiratory portion of the cycle. This and many other procedures involving sampling the respiratory flow rate Qr produce measures which are broadly proportional to ventilation, provided the flow rate waveform shape does not vary very much (here, the shape of two breaths is taken to be similar when the flow rate waveforms of the breaths normalised in time and amplitude are similar). Some simple examples include the median positive respiratory flow rate, the median of the absolute value of respiratory flow rate, and the standard deviation of flow rate. Arbitrary linear combinations of arbitrary order statistics of the absolute value of respiratory flow rate using positive coefficients, and even some using both positive and negative coefficients, are approximately proportional to ventilation. Another example is the mean of the respiratory flow rate in the middle K proportion (by time) of the inspiratory portion, where 0<K<1. There is an arbitrarily large number of measures that are exactly proportional to ventilation if the flow rate shape is constant.

5.4.3.2.4 Determination of Inspiratory Flow Limitation

In one form of the present technology, the central controller 4230 executes an inspiratory flow limitation determination algorithm 4324 for the determination of the extent of inspiratory flow limitation.

In one form, the inspiratory flow limitation determination algorithm 4324 receives as an input a respiratory flow rate signal Qr and provides as an output a metric of the extent to which the inspiratory portion of the breath exhibits inspiratory flow limitation.

In one form of the present technology, the inspiratory portion of each breath is identified by a zero-crossing detector. A number of evenly spaced points (for example, sixty-five), representing points in time, are interpolated by an interpolator along the inspiratory flow rate-time curve for each breath. The curve described by the points is then scaled by a scalar to have unity length (duration/period) and unity area to remove the effects of changing breathing rate and depth. The scaled breaths are then compared in a comparator with a pre-stored template representing a normal unobstructed breath, similar to the inspiratory portion of the breath shown in FIG. 4. Breaths deviating by more than a specified threshold (typically 1 scaled unit) at any time during the inspiration from this template, such as those due to coughs, sighs, swallows and hiccups, as determined by a test element, are rejected. For non-rejected data, a moving average of the first such scaled point is calculated by the central controller 4230 for the preceding several inspiratory events. This is repeated over the same inspiratory events for the second such point, and so on. Thus, for example, sixty five scaled data points are generated by the central controller 4230, and represent a moving average of the preceding several inspiratory events, e.g., three events. The moving average of continuously updated values of the (e.g., sixty five) points are hereinafter called the "scaled flow rate", designated as Qs(t). Alternatively, a single inspiratory event can be utilised rather than a moving average.

From the scaled flow rate, two shape factors relating to the determination of partial obstruction may be calculated.

Shape factor 1 is the ratio of the mean of the middle (e.g. thirty-two) scaled flow rate points to the mean overall (e.g. sixty-five) scaled flow rate points. Where this ratio is in excess of unity, the breath will be taken to be normal. Where the ratio is unity or less, the breath will be taken to be obstructed. A ratio of about 1.17 is taken as a threshold between partially obstructed and unobstructed breathing, and equates to a degree of obstruction that would permit maintenance of adequate oxygenation in a typical patient.

Shape factor 2 is calculated as the RMS deviation from unit scaled flow rate, taken over the middle (e.g. thirty two) points. An RMS deviation of about 0.2 units is taken to be normal. An RMS deviation of zero is taken to be a totally flow-limited breath. The closer the RMS deviation to zero, the breath will be taken to be more flow limited.

Shape factors 1 and 2 may be used as alternatives, or in combination. In other forms of the present technology, the number of sampled points, breaths and middle points may differ from those described above. Furthermore, the threshold values can be other than those described.

5.4.3.2.5 Determination of Apneas and Hypopneas

In one form of the present technology, the central controller 4230 executes an apnea/hypopnea determination algorithm 4325 for the determination of the presence of apneas and/or hypopneas.

In one form, the apnea/hypopnea determination algorithm 4325 receives as an input a respiratory flow rate signal Qr and provides as an output a flag that indicates that an apnea or a hypopnea has been detected.

In one form, an apnea will be said to have been detected when a function of respiratory flow rate Qr falls below a flow rate threshold for a predetermined period of time. The function may determine a peak flow rate, a relatively short-term mean flow rate, or a flow rate intermediate of relatively short-term mean and peak flow rate, for example an RMS flow rate. The flow rate threshold may be a relatively long-term measure of flow rate.

In one form, a hypopnea will be said to have been detected when a function of respiratory flow rate Qr falls below a second flow rate threshold for a predetermined period of time. The function may determine a peak flow, a relatively short-term mean flow rate, or a flow rate intermediate of relatively short-term mean and peak flow rate, for example an RMS flow rate. The second flow rate threshold may be a relatively long-term measure of flow rate. The second flow rate threshold is greater than the flow rate threshold used to detect apneas.

5.4.3.2.6 Determination of Snore

In one form of the present technology, the central controller 4230 executes one or more snore determination algorithms 4326 for the determination of the extent of snore.

In one form, the snore determination algorithm 4326 receives as an input a respiratory flow rate signal Qr and provides as an output a metric of the extent to which snoring is present.

The snore determination algorithm 4326 may comprise the step of determining the intensity of the flow rate signal in the range of 30-300 Hz. Further, the snore determination algorithm 4326 may comprise a step of filtering the respiratory flow rate signal Qr to reduce background noise, e.g., the sound of airflow in the system from the blower.

5.4.3.2.7 Determination of Airway Patency

In one form of the present technology, the central controller 4230 executes one or more airway patency determination algorithms 4327 for the determination of the extent of airway patency.

In one form, the airway patency determination algorithm 4327 receives as an input a respiratory flow rate signal Qr, and determines the power of the signal in the frequency range of about 0.75 Hz and about 3 Hz. The presence of a peak in this frequency range is taken to indicate an open airway. The absence of a peak is taken to be an indication of a closed airway.

In one form, the frequency range within which the peak is sought is the frequency of a small forced oscillation in the treatment pressure Pt. In one implementation, the forced oscillation is of frequency 2 Hz with amplitude about 1 $cmH_2O$.

In one form, airway patency determination algorithm 4327 receives as an input a respiratory flow rate signal Qr, and determines the presence or absence of a cardiogenic signal. The absence of a cardiogenic signal is taken to be an indication of a closed airway.

5.4.3.2.8 Determination of Target Ventilation

In one form of the present technology, the central controller 4230 takes as input the measure of current ventilation, Vent, and executes one or more target ventilation determination algorithms 4328 for the determination of a target value Vtgt for the measure of ventilation.

In some forms of the present technology, there is no target ventilation determination algorithm 4328, and the target value Vtgt is predetermined, for example by hard-coding during configuration of the RPT device 4000 or by manual entry through the input device 4220.

In other forms of the present technology, such as adaptive servo-ventilation (ASV), the target ventilation determination algorithm 4328 computes a target value Vtgt from a value Vtyp indicative of the typical recent ventilation of the patient.

In some forms of adaptive servo-ventilation, the target ventilation Vtgt is computed as a high proportion of, but less than, the typical recent ventilation Vtyp. The high proportion in such forms may be in the range (80%, 100%), or (85%, 95%), or (87%, 92%).

In other forms of adaptive servo-ventilation, the target ventilation Vtgt is computed as a slightly greater than unity multiple of the typical recent ventilation Vtyp.

The typical recent ventilation Vtyp is the value around which the distribution of the measure of current ventilation Vent over multiple time instants over some predetermined timescale tends to cluster, that is, a measure of the central tendency of the measure of current ventilation over recent history. In one implementation of the target ventilation determination algorithm 4328, the recent history is of the order of several minutes, but in any case should be longer than the timescale of Cheyne-Stokes waxing and waning cycles. The target ventilation determination algorithm 4328 may use any of the variety of well-known measures of central tendency to determine the typical recent ventilation Vtyp from the measure of current ventilation, Vent. One such measure is the output of a low-pass filter on the measure of current ventilation Vent, with time constant equal to one hundred seconds.

5.4.3.2.9 Determination of Therapy Parameters

In some forms of the present technology, the central controller 4230 executes one or more therapy parameter determination algorithms 4329 for the determination of one or more therapy parameters using the values returned by one or more of the other algorithms in the therapy engine module 4320.

In one form of the present technology, the therapy parameter is an instantaneous treatment pressure Pt. In one implementation of this form, the therapy parameter determination algorithm 4329 determines the treatment pressure Pt using the equation $$Pt = A\Pi(\Phi, t) + P_0 \quad (1)$$

where:
A is the amplitude,
$\Pi(\Phi, t)$ is the waveform template value (in the range 0 to 1) at the current value $\Phi$ of phase and t of time, and
$P_0$ is a base pressure.

If the waveform determination algorithm 4322 provides the waveform template $\Pi(\Phi, t)$ as a lookup table of values $\Pi$ indexed by phase $\Phi$, the therapy parameter determination algorithm 4329 applies equation (1) by locating the nearest lookup table entry to the current value $\Phi$ of phase returned by the phase determination algorithm 4321, or by interpolation between the two entries straddling the current value $\Phi$ of phase.

The values of the amplitude A and the base pressure $P_0$ may be set by the therapy parameter determination algorithm 4329 depending on the chosen respiratory pressure therapy mode in the manner described below.

5.4.3.3 Therapy Control Module

The therapy control module 4330 in accordance with one aspect of the present technology receives as inputs the therapy parameters from the therapy parameter determination algorithm 4329 of the therapy engine module 4320, and controls the pressure generator 4140 to deliver a flow of air in accordance with the therapy parameters.

In one form of the present technology, the therapy parameter is a treatment pressure Pt, and the therapy control module 4330 controls the pressure generator 4140 to deliver a flow of air whose mask pressure Pm at the patient interface 3000 is equal to the treatment pressure Pt.

5.4.3.4 Detection of Fault Conditions

In one form of the present technology, the central controller 4230 executes one or more methods 4340 for the detection of fault conditions. The fault conditions detected by the one or more methods 4340 may include at least one of the following:
Power failure (no power, or insufficient power)
Transducer fault detection
Failure to detect the presence of a component
Operating parameters outside recommended ranges (e.g. pressure, flow rate, temperature, $PaO_2$)
Failure of a test alarm to generate a detectable alarm signal.

Upon detection of the fault condition, the corresponding algorithm 4340 signals the presence of the fault by one or more of the following:
Initiation of an audible, visual &/or kinetic (e.g. vibrating) alarm Sending a message to an external device Logging of the incident

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller 4230. One example of an air circuit 4170 comprising a heated wire circuit is described in U.S. Pat. No. 8,733,349, which is incorporated herewithin in its entirety by reference.

5.5.1 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.6 Humidifier

5.6.1 Humidifier Overview

In one form of the present technology there is provided a humidifier 5000 (e.g., as shown in FIG. 5C) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

RPT Device and Humidifier

FIGS. 6A and 6B illustrate an integrated RPT device and humidifier 6000 according to an example of the present technology. As illustrated, the integrated RPT device and humidifier 6000 includes a reservoir dock 6050 structured and arranged to receive a water reservoir 6100 (also referred to as a humidifier tub or a humidifier reservoir). In the illustrated example, the integrated RPT device and humidifier 6000 comprises a humidifier that is integrated with an RPT device such that a pneumatic block of the RPT device comprises components that perform the function of the RPT device as well as components that perform the function of the humidifier.

It should be appreciated that the humidifier (e.g., reservoir dock 6050) may be provided separately to the RPT device in an alternative arrangement. In such arrangement, additional interfaces may be used to connect the humidifier (e.g., reservoir dock 6050) to the RPT device.

The RPT device comprises a blower supported within the pneumatic block. The blower is structured and arranged for producing a flow, or a supply, of air at positive pressure, e.g., in the range of 2-50 cmH$_2$O. In an example, the blower may include a single stage design or a multi-stage design, e.g., two or more stage designs. The blower is operable to draw a supply of air into the pneumatic block, e.g., through one or more intake openings in the pneumatic block, and into an inlet thereof (blower inlet), and provide a pressurized supply of air at an outlet (blower outlet). Examples and details of an exemplary blower are described in PCT Patent Application Publication No. WO 2013/020167, which is incorporated herein by reference in its entirety. The blower outlet is communicated with the humidifier, e.g., an inlet of the water reservoir 6100.

5.6.2 Humidifier Components

5.6.2.1 Water Reservoir

FIGS. 6A and 6B show a water reservoir 6100 according to an example of the present technology. The water reservoir 6100 is configured to hold, or retain, a volume of liquid (e.g. water) to be evaporated for humidification of the flow of air. The water reservoir 6100 may be configured to hold a predetermined maximum volume of water in order to provide adequate humidification for at least the duration of a respiratory therapy session, such as one evening of sleep. Typically, the water reservoir is configured to hold several hundred millilitres of water, e.g. 300 millilitres (ml), 325 ml, 350 ml or 400 ml, although it is to be understood that other volumes of liquid may be utilised, e.g., at least 100 ml. In other forms, the humidifier may be configured to receive a supply of water from an external water source such as a building's water supply system.

According to one aspect, the water reservoir 6100 is configured to add humidity to a flow of air from the RPT device as the flow of air travels therethrough. In one form, the water reservoir 6100 may be configured to encourage the flow of air to travel in a tortuous path through the reservoir while in contact with the volume of water therein. For example, the water reservoir 6100 may comprise one or more flow elements, e.g., baffles, to encourage a tortuous flow path.

The water reservoir 6100 may be removably coupled with the reservoir dock 6050. In an example, insertion/removal of the water reservoir may be provided along a path extending in an anterior-posterior direction. In an alternative example, at least a portion of the path for insertion/removal of the water reservoir may extend in an inferior-superior direction, e.g., at least a portion of the path for insertion includes a slope or drop down into an operative position.

The water reservoir 6100 may also be configured to discourage egress of liquid therefrom, such as when the reservoir is displaced and/or rotated from its normal, working orientation, such as through any apertures and/or in between its sub-components. As the flow of air to be humidified by the humidifier is typically pressurised, the reservoir may also be configured to prevent losses in pneumatic pressure through leak and/or flow impedance.

5.6.2.2 Humidifier Transducer(s)

The humidifier 5000 may comprise one or more humidifier transducers (sensors) 5210 instead of, or in addition to, transducers 4270 described above. Humidifier transducers 5210 may include one or more of an air pressure sensor 5212, an air flow rate transducer 5214, a temperature sensor 5216, or a humidity sensor 5218 as shown in FIG. 5G. A humidifier transducer 5210 may produce one or more output signals which may be communicated to a controller such as the central controller 4230 and/or the humidifier controller 5250. In some forms, a humidifier transducer may be located externally to the humidifier 5000 (such as in the air circuit 4170) while communicating the output signal to the controller.

5.6.2.2.1 Pressure Transducer

One or more pressure transducers 5212 may be provided to the humidifier 5000 in addition to, or instead of, a pressure sensor 4272 provided in the RPT device 4000.

5.6.2.2.2 Flow Rate Transducer

One or more flow rate transducers 5214 may be provided to the humidifier 5000 in addition to, or instead of, a flow rate sensor 4274 provided in the RPT device.

5.6.2.2.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet. In some forms, the humidifier 5000 may further comprise a temperature sensor 5216 to detect the temperature of the ambient air.

5.6.2.2.4 Humidity Transducer

In one form, the humidifier 5000 may comprise one or more humidity sensors 5218 to detect a humidity of a gas, such as the ambient air. The humidity sensor 5218 may be placed towards the humidifier outlet in some forms to measure a humidity of the gas delivered from the humidifier 5000. The humidity sensor may be an absolute humidity sensor or a relative humidity sensor.

5.6.2.3 Heating Element

As shown in FIG. 6B, a heater plate 6080 is used to transfer heat to the water reservoir. In the illustrated example, the heater plate may form a part of the reservoir dock 6050, and may be located on or near the base of the reservoir dock. At least the top layer of the heater plate comprises a hard scratch resistant surface that may be formed, for example, of a nickel chrome alloy, stainless steel or anodised aluminium. The heater plate may transfer heat from a heating element. The heating element may comprise a heat generating component such as an electrically resistive heating track. One suitable example of a heating element is a layered heating element such as one described in the PCT Patent Application Publication No. WO 2012/171072, which is incorporated herewith by reference in its entirety.

The thermal pad is preferably made by a pliable or compliant thermo-conductive material and is arranged between the heater plate 6080 and the heating element 6085 (e.g., engages or sticks (e.g., bonds) to both the heater plate and the heating element). In this arrangement, the thermal pad can fill the air gaps or spaces between heater plate 6080 and the heating element 6085, which enhances thermal conductivity from the heating element 6085 to the heater plate 6080. As both the heater plate 6080 and the heating element 6085 typically include planar surfaces made of a hard material, any small imperfections on the surfaces may cause air gaps between these two surfaces. Having the pliable layer between these surfaces helps with removing such air gaps and improving the thermal conductivity of the system.

5.6.2.4 Humidifier Controller

According to one arrangement of the present technology, a humidifier 5000 may comprise a humidifier controller 5250 as shown in FIG. 5G. In one form, the humidifier controller 5250 may be a part of the central controller 4230. In another form, the humidifier controller 5250 may be a separate controller, which may be in communication with the central controller 4230.

In one form, the humidifier controller 5250 may receive as inputs measures of properties (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5G, the humidifier controller 5250 may comprise one or more controllers, such as a central humidifier controller 5251, a heated air circuit controller 5254 configured to control the temperature of a heated air circuit 4171 and/or a heating element controller 5252 configured to control the temperature of a heating element 5240.

5.6.3 Wire Cross-Talk

In an example, the air delivery tube 4170 may include a plurality of wires helically wound around the axis of the air delivery tube 4170 (e.g., along the tube portion of the air delivery conduit 4170), e.g., configured to heat air in the air delivery tube and/or transmit signals from one or more transducers (e.g., temperature sensor, flow sensor) to a controller of the RPT device.

In an example, the air delivery tube 4170 may comprise four wires, e.g., two wires for powering one or more heating elements and two wires for connecting a sensor 9030 (e.g., temperature sensor/transducer). However, it should be appreciated that other numbers of wires may be used, e.g., two wires, three wires, or five or more wires. In some examples, one or more other sensors may be provided in the air delivery tube 4170 and/or outside of the air delivery tube 4170 (e.g., part of the patient interface) with wiring for the one or more sensors routed along the air delivery tube 4170.

In an example, the air delivery tube 4170 includes a dock connector 4600 with a contact assembly including contacts that, in use, are engaged with respective contacts provided to the reservoir dock 6050 to form electrical connections with the reservoir dock at the dock outlet to provide electrical power and/or control signal transmission. In an example, the contacts of the dock connector may be joined to respective wires running along the air delivery tube 4170. In an alternative example, the at least some of the contacts are not related to the wires running along the air delivery tube 4170, but are characterised by their own independent and/or unique electrical characteristics (e.g., resistance, conductance, etc.). Such independent and/or unique electrical characteristics may be used for identifying one or more elements of the tube/patient interface system, or of characteristics of these elements.

The heating wires are usually distributed along the length of the tube and the sensor is usually positioned at the mask end of the tube. Thus, both the heating wires and the sensor connecting wires may extend the length of the tube.

As noted above, the air delivery tube 4170 according to an example of the present technology may comprise four wires, e.g., two wires for heating elements and two wires for a transducer, e.g., negative temperature coefficient (NTC) thermistor used as a temperature sensor. It should be noted that NTC is only one of a plurality of different types of temperature sensors known to a skilled addressee. When multiple wires are routed along the length of the air delivery tube 4170, cross-talk between the wires may cause errors in measurements of the transducer.

An aspect of the present technology relates to reducing or eliminating cross-talk between wires, e.g., to enhance accuracy of the signal transmission provided by the NTC thermistor.

FIG. 7 shows a schematic view of a tube with a four wire circuit coupled to a dock in accordance with one form of the present technology. In the four wire configuration, two connections (−PWM and GND) can be coupled to a heater control circuit and two connections (VH and VL) can be coupled to a sensing circuit. The sensing circuit connections may be coupled to a sensor 9030 and the heater control circuit coupled to heating elements in the tube 4170.

The heater control circuit may supply power to heating element in the tube 4170 via a switch (e.g., a transistor). The heater control circuit may control the duration, voltage, and/or frequency and/or period of Pulse Width Modulation (PWM) signal supplied to the heating elements in the tube 4170.

The sensing circuit may be configured to receive signal(s) from a transducer (e.g., negative temperature coefficient (NTC) thermistor) disposed in the tube 4170, indicative of the operation of the heating elements in the tube 4170. The sensing circuit may control a sensor power source to provide intermittently power to the sensor in order to detect a connection of the tube, and keep the sensor power source on, when it is detected that the tube is connected to the humidifier. The transducer may be disposed at the mask proximal end) of the tube. For example, the sensing circuit may measure voltage and/or current of the transducer to determine the operating characteristics (e.g., temperature) of the heating elements. The heater control circuit may control the heating elements based on the signals received by the sensing circuit and the settings sets for the heating tube 4170. Other sensors disposed anywhere in the tube, i.e., humidity sensors, may also be connected in a similar way.

In some examples, the sensing circuit may automatically identify the type of tube 4170 connected to the dock 6050. The type of tube that is connected to the dock 6050 may be determined by the sensing circuit based on unique electrical characteristic(s) provided by active and/or passive components in the tube 4170 via one or more of the four electrical connectors. Based on the indicated type of tube 4170 connected to the dock, a controller may change the operating parameter of the system. For example, different heating control settings may be provided for different tubes (e.g., non-heated tube, heated tube, tube with heat and moisture exchanger (HME), tube unknown). In some example, the settings may be modified based on the size of the identified air delivery tube (e.g., 15 mm, 19 mm), presence and type of HME, type of patient interface connected to tube, etc. The type of tube that is connected to the dock 6050 may be determined by the sensing circuit based on unique electrical characteristic(s) provided by active and/or passive components in the tube 4170 via one or more of the four connectors.

In the four wire circuit shown in FIG. 7, resistors 9010 and 9012 represent resistance of the one or more heating element/s and resistors 9020 and 9022 represent the resistance of the wires coupled to a sensor 9030. FIG. 7 is a schematic representation and the fact that two set of resistors 9010 and 9012 are shown does not necessarily mean that there are two or more heater wires. A single continuous heating wire or more than two wires may also be used in the discussed heated tubes. For example, the two-wire arrangement shown in FIG. 7 has four connections formed between the dock and the tube. PWM and GND connections are coupled to the heating element/s and VH and VL are coupled to the sensor 9030. The capacitance elements C shown in FIG. 7 are not actual capacitors, but represent the distributed parasitic capacitive coupling between two wires (i.e. between the heater wire 9010 and the resistor wire 9020) located in close proximity For the heating element/s, the power is supplied via connections PWM and GND and may be regulated by a Pulse Width Modulator (PWM). The PWM signal creates an AC signal. Certain settings (e.g., pulse frequency) of the PWM signal may cause the heating element wires to move/vibrate (which can be audible) due to electromagnetics (EM). To prevent hearing the movement of the wires, the pulse frequencies of the PWM signal may be set at and/or above a predetermined value above human perception threshold frequency (e.g., at or above 20 KHz).

The sensor 9030 may be a transducer (e.g., a negative temperature coefficient (NTC) thermistor) disposed in the tube 4170 for measuring the heat in the tube 4170. As discussed above, the sensor 9030 may have different characteristics (e.g., nominal resistance values of 10K or a 100 k @ 25° C.) to identify different types of tubes. At room temperature the sensor 9030 may have a resistance value (e.g., tens of K Ohms) that is significantly larger than a resistance of wires (e.g., 5 Ohms) connected to the sensor 9030. The two values of the nominal resistance that are mentioned above are chosen so as to avoid, or minimise, any overlap between the resistance ranges exhibited by the respective sensors during normal or even extreme temperature variations. For example, in a temperature range of say −4° C. to 40° C., an NTC thermistor of nominal resistance value of 10K (at 25° C.) may exhibit a range of resistances that vary from low-to-mid tens of K to several K (see FIG. 12). In contrast, in a temperature range of say −4° C. to 40° C., an NTC thermistor of nominal resistance value of 100K (at 25° C.) may exhibit a range of resistances varying from hundreds of K to high tens of K. Only at extreme temperatures there may be some minimal overlap between the exhibited resistance (say negative temperatures for the 10K, and well above 40° C. for the 100 k.

As shown schematically in FIG. 9, voltage Vsense is provided to the sensor 9030. The voltage is provided by the microcontroller via a divider network comprising a first resistor RHigh and a second resistor RLow. The sensor 9030 is coupled with the two resistors RLow and RHigh so that, upon failure of one of the wires, the system can detect which wire failed. A DC voltage is applied to the divider network for detecting the operating parameters of the sensor 9030 and/or failure of one of the wires. The combination of measured voltages at the VLow and VHigh terminals would indicate to a skilled addressee whether an NTC wire is shortened with another NTC wire, or with a heater wire, and also with which exactly heater wire. For example, an NTC wire shortened with an NTC wire the microcontroller will measure a zero voltage difference. On the other hand, if the NTC wire has short-circuited with a PWM heater wire, the measured voltage difference in some cases may be larger than Vsense (the Vsense DC voltage is usually about 3.3V, whilst the PWM AC voltage is about 24V).

In operation, when the PWM pulse is turned on, the PWM wires are capacitively connected (see capacitors C in FIG. 7) to the wires of the sensor 9030. The AC signal penetrates through the parasitic (inherent) capacitors into the sensor wires (e.g., represented by resistors 9020 and 9022). FIG. 8 shows a signal diagram of a PWM signal that may be applied to the heating elements (Signal (A) or (B)) and the portions of the PWM induced signal that may be observed in the sensing circuit (Signal (C)), in response to the application of signal (B) to the PWM line.

The signal at VH (V high) and VL (V low) points is provided to the microcontroller configured to subtract the V low from the V high. The difference between the V low and V high indicates the resistance of the sensor 9030. The microprocessor is configured to track the changes in resistance of the sensor 9030 due to changes in the temperature of the tube 4170 and determine operation setting for components of the system (e.g., heating elements in the tube 4170).

The probing of the sensor 9030 (e.g., by a microprocessor) may be timed at intervals that are not synchronized with the PWM signal. In some examples, the probing of the sensor 9030 is slower than the period of the PWM signal. In some instances, the probing period may be several seconds. The probing period may change depending on the circumstances. For example, in some instances the probing may be constant, whilst in others, a probing of several seconds may be used for the time periods when it is detected that there is no tube connected to the dock, however a shorter period, or even a continuous monitoring, may be used once it is detected that there is a tube connected to the device. As discussed above, the signal for probing the sensor 9030 is provided as a DC signal.

Because of the slow probing of the sensor 9030, the sensing circuit can catch different portion of the fast PWM induced signal (see graph (c) of FIG. 8). The induced signal may be 10-20 percent of the voltage of the sensor 9030 signal. The setting of the PWM signal and changes in the PWM signal may affect the accuracy of the measurement based on the voltage of the sensor 9030 signal. The temperature error caused in the sensing circuitry may be up to 5 degrees (in a measured range of 5 to 40 degrees) and possibly higher, depending on construction and/or topology of the wires in the heated tube.

To address these issues, in accordance with one form of the present technology, high pass electrical filters are provided between the NTC output Vhigh and Vlow points and ground, to remove the high frequency components of the signal (those of PWM frequency and above) in the circuity including the sensor 9030. As shown in FIG. 9, a first high pass filter HPF1 is coupled to the RHigh resistor and ground and a second high pass filter HPF2 is coupled to the Rlow resistor and ground. Filters HPF1 and HPF2 pass (shunt) the high PWM frequencies to ground, thus allowing only the desired low frequencies to remain at points VH and VL.

Alternatively, or in addition to the above high pass shunt filters, low pass electrical filters (e.g., LPF3 and/or LPF4) can be provided between the NTC output VH and VL points and the microcontroller. As shown in FIG. 9, a first low pass filter LPF3 is coupled to the RHigh resistor and connection VH-Lpf and a second low pass filter LPF4 is coupled to the Rlow resistor and the connection VL-Lpf. Each filter (HPF1, HPF2, LPF3, LPF4) may be formed by a single component (i.e., a capacitor) or a combination of active (i.e., operational amplifiers) and/or passive (resistor/capacitors) electronic components. For example, when a large capacitor (tens of nF) is used for each of HPF1 and HPF2, the cross-talk between the wires of the heated tube and the sensor may be largely mitigated even without the use of LPF3 and/or LPF4. However, the use of smaller capacitors for HPF1 and HPF2, may be less expensive, as well as, in some cases, be preferable from the point of view of a general EMC (electromagnetic compatibility) compliance of the circuit and the entire device. For example, in some instances, the values of about several tens of pF are found to be preferred, in order to better accommodate the EMC compliance of the device. So when smaller capacitor values (i.e., tens of pF) are used for HPF1 and HPF2, these two filters may be more useful for removing the emissions of higher frequencies, but may not mitigate the cross-talk efficiently at selected frequency of 20 KHz. This can be compensated with the introduction of LPF3 and LPF4 which may be configured to filter frequencies near the frequencies of the pulse width modulated power signal and frequencies higher than the frequencies of the pulse width modulated power signal. Filters LPF3 and LPF4 are preferably designed to include active components in order to improve the filter roll off slope and the desired attenuation (i.e. at 20 kHz) of the frequency response of the filter. Standard design tools are available to design a filter with the desired cut-off frequency and attenuation at the target frequency.

The sensor 9030 supply (for the divider) Vsense can be turned on and off to detect if the tube 4170 connected. When the tube 4170 is not connected, the supply to the sensor 9030 can be turned off. Turning off the supply may reduce corrosion in the connections.

In accordance with one form of the present technology, the sensor 9030 supply (for the divider) Vsense is generally turned off, but is turned on and off periodically to detect if the tube 4170 is connected. When it is detected that the tube 4170 is not connected, the supply to the sensor 9030 is turned off again. Turning off the supply may reduce corrosion in the connections in the humid environment in which they may be operating. During the short periods the tube is intermittently turned on, the check on whether the tube has been attached, is conducted by probing VH and VL. If VH=Vsense and VL=0, the tube is not connected. If the tube has been connected, because of the voltage divider defined by RH and RL, VH and VL change to respective voltages that are within a predetermined range. When the tube is detected, Vsense is switched on permanently and VH and VL are used to measure the temperature.

The turning on and off of Vsense may be controlled to happen at intervals that are greater than the period of the PWM signal applied to the heating elements. In one example, the frequency of the PWM signal may be 20 KHz (T=50 µs) and the Vsense is turned on and off every 1, 2, or 3 seconds (1 to 0.333 Hz). If other, including non-periodical, time ranges are employed for the intermittent turning on of Vsense, to effect the probing for the connection of the heated tube, they are likely to be of similar frequency range. Therefore, the filters HPF1, HPF2, LPF3 and/or LPF3 may be configured to filter out the cross-talk (20 KHz), but keep the respective transient (1, 2, or 3 seconds) from the on and off operation, and any fast changes in the sensor 9030 (e.g., an open window). In one example, the filters may be configured to filter out everything above several Hz. In other examples the filter may filter everything above any one chosen frequency in the frequency range of 1 to 100 Hz.

Alternatively, in a system where the EMC is resolved by other means and/or is not an issue, filters LPF3 and LPF4 may be sufficient on their own to mitigate the cross-talk issues of the system. However, it has been found that for the most practical application, HPF1 and HPF2 filters were really necessary for addressing the EMC problems.

While the above examples of the present technology have been described with reference to a four wire system, the examples are not so limited. The examples of the present technology may be applied to systems with other number of wires, e.g., two wires, three wires, or five or more wires.

5.7 Tube Identification Examples

FIG. 10A shows a schematic view of a dock and a tube connection in accordance with one form of the present technology. The dock outlet 6090 may include a contact assembly 6800 that can be coupled to a corresponding contact assembly 4172 of the tube 4170 via four connections. The dock outlet 6090 may be mechanically and electrically coupled to the tube 4170.

As shown in FIG. 10A, the contact assembly 6800 includes four connections that are coupled to processing circuitry, e.g., PCBA 7600. Two of the connections (Heater+ and Heater−) are coupled to a heater control circuit and two of the connections (+SENSOR and −SENSOR) are coupled to a sensing circuit. In some examples, the +SENSOR and −SENSOR connections may be coupled to an NTC sensor. In some examples, the sensing circuit may also be connected to the connections (Heater+ and Heater−). The heater control circuit and the sensing circuit may be included in the humidifier, e.g., PCBA 7600.

The heater control circuit may supply power to heating element in the tube 4170 via a switch (e.g., a transistor). The heater control circuit may control the duration, voltage, and/or frequency and/or period of Pulse Width Modulation (PWM) signal supplied to the heating elements in the tube 4170.

The sensing circuit may be configured to receive signal(s) from a transducer (e.g., negative temperature coefficient (NTC) thermistor) disposed in the tube 4170, indicative of the operation of the heating elements in the tube 4170. The transducer may be disposed at the mask proximal end of the tube.

For example, the sensing circuit may measure voltage and/or current of the transducer to determine the operating characteristics (e.g., temperature) of the heating elements. The heater control circuit may control the heating elements based on the signals received by the sensing circuit and the settings sets for the heating tube 4170. Other sensors disposed anywhere in the tube, i.e., humidity sensors, may also be connected in a similar way.

The sensing circuit may automatically identify the type of tube 4170 connected to the dock 6050. The type of tube that is connected to the dock 6050 may be determined by the sensing circuit based on unique electrical characteristic(s)

provided by active and/or passive components in the tube 4170, or adaptors attached to the tube, via one or more of the four electrical connectors 6805. Based on the indicated type of tube 4170 connected to the dock, a controller may change the operating parameter of the system. For example, different heating control settings may be provided for different tubes (e.g., non-heated tube, heated tube, tube with heat and moisture exchanger (HME), tube unknown). In some example, the settings may be modified based on the size of the identified air delivery tube (e.g., 15 mm, 19 mm), presence and type of HME, type of patient interface connected to tube, etc. The type of tube that is connected to the dock 6050 may be determined by the sensing circuit based on unique electrical characteristic(s) provided by active and/or passive components in the tube 4170 via one or more of the four connectors.

As shown in FIG. 10A, the tube 4170 includes four connections for coupling to respective four connections in the contact assembly 6800. The connections in the tube may be solid pins, but are not so limited. In some examples, the connections may be provided by, for example, leadframe terminals. In one example, when the tube 4170 is connected to the dock, solid pins in one of the devices connect to corresponding pogo pins in the other device.

As shown in FIG. 10A, a first circuit element 8022 is coupled to two pins in tube 4170 and a second circuit element 8024 is coupled to two other pins in the tube 4170. While single circuit elements are shown in FIG. 10A, first and/or circuit elements may include a plurality of active and/or passive circuit elements.

The first circuit element 8022 may include the heater elements in the tube 4170 and/or one or more other elements. The first circuit element 8022 may represent the resistance of the heater elements.

The second circuit element 8024 may include a sensor in the form of a thermistor formed of a Negative Temperature Coefficient (NTC) material. The parameters of the second circuit element 8024 (e.g., resistance) may change with a change of tube temperature. The sensing circuit may be configured to sense the temperature of the tube 4170 by monitoring changes in the parameters of the second circuit element 8024.

FIG. 10B shows circuit diagram of the dock and tube connection in accordance with one form of the present technology. The first circuit element 8022 in FIG. 10A may be represented by two resistors SR (with approximately 5 ohms) coupled to the Heater+ and Heater− connections. This is associated with the fact that the heating wire usually comprises one or more (usually two) copper wires connected sequentially to each other and having a total resistance of about 10 ohms. The combined length of wire extends from the dock coupling end of the tube to the mask coupling end of the tube and back to the dock coupling end of the tube. The second circuit element 8024 in FIG. 10A may be represented by a thermistor and two resistors SR coupled to the NTC+ and NTC− connections. The thermistor in FIG. 10A may be selected based on the type of air tube. A 10 k thermistor may be provided in a 15 mm air tube, a 100 k thermistor may be provided in a 19 mm air tube, and an open circuit may be provided in a passive air tube.

The heating wires 8022 are usually distributed along the length of the tube and the sensor 8024 is usually positioned at the mask end of the tube. Thus, both the heating wires and the sensor connecting wires extend the length of the tube.

The first and second circuit elements may be used by the sensing circuit to identify the type of tube connected to the dock 6050. In some examples, unique electrical characteristic of one or more contact pins may be used to identify parameters of the tube. The different resistance values provided by the first and second circuit elements may allow for the control circuit in the humidifier to determine the type of tube that is connected and which control parameters to use for the operation of the system. The sensing circuit may measure the resistance of the first circuit element and/or the second circuit element to determine the type of tube. Alternatively, further electrical pins (in addition to the four pins illustrated in FIGS. 10 and 11) may be included in the dock connector 4600 of the air delivery tube 4170, which are associated with a unique characteristic (such as electrical resistance) and may be used to indicate parameters such as the type, as well as other characteristics associated with the tube.

As an example, the different type of tubes may include: (1) a 4-wire 15 mm heated tube may provide a Heater Wire resistance of 2×5R and a NTC resistance value at 25° C. is 10K; (2) a 4-wire 19 mm heated tube may provide a Heater Wire resistance is 2×5R and NTC resistance value at 25° C. is 100K; and (3) a passive non-heated tube may be provided with a standard ISO-taper.

Thus the detection of the connected tube type is performed by measuring the second circuit element (e.g., NTC) and the first circuit element (e.g., Heater Wire) resistance combinations (in cases (1) and (2) above), detecting the electrical characteristics of one or more independent pins or a combination of such, or detecting the open circuit on both pairs of connections (case (3) above).

The system may also be configured to automatically detect a single fault conditions in the connected active tube, for example short or open circuit on any of the four tube wires, as well as the non-legit value (partial crack) of the Heater Wire, as well as cross-short circuit between the tube wires.

Examples of the present technology provides not only for direct coupling of a tube to the dock, but also for an electrical adapter. While such an adaptor may allow the connection to the dock of different types of heated wire tube, its main purpose is to facilitate the coupling to the dock of a passive air tube capable of operating with or without HME passive humidifier at the proximal end. The two main applications for using such adapter are: (a) allowing the mechanical connection of passive air tubes to the dock and (b) providing the means for the system to detect the passive air tube.

FIG. 11 shows a schematic view of a dock and a tube connection in accordance with the above discussed form of the present technology. As shown in FIG. 11, the contact assembly 6800 of the dock may be coupled to a passive tube 4170 via an adapter 8020. The adaptor 8020 provides an electrical connection, which is generally not present in the passive tube 4170, to the contact assembly 6800 of the dock. In one example, the tube 4170 may provide a mechanical connection to the dock 6050 and the tube adaptor 8020 may provide the electrical connection. In some examples, the tube adaptor 8020 may also mechanically couple to the dock.

In some examples, the adaptor 8020 may be part of a contact assembly. The adaptor 8020 may be manufactured as an integral part of the tube 4170 or be removable from the tube 4170. In this manner air tubes that do not have electrical components, such as heating elements and/or sensors, may be provided with circuit elements to identify the kind of air tube that is connected to the dock 6050.

In contrast to FIG. 10A including the first and second circuit elements 8022 and 8024 in the tube 4170, the example shown in FIG. 11 includes the first and second circuit elements 8022 and 8024 in the adapter. Only in this case these circuit elements do not represent the resistance of a heater wire and of a NTC sensor/transducer, but include simple resistors that are detected by the controller in order to identify the connection of a passive tube to the system. The first and second circuit elements 8022 and 8024 may be provided in a housing including the connections. The first and second circuit elements 8022 and 8024 may directly connect to the connections provided in the adaptor 8020. In one example, the first circuit element 8022 includes a single resistor which is directly coupled to two of the connections in the adapter of the tube, and the second circuit element 8024 includes a single resistor which is directly coupled to two other connections in the adapter of the tube. In some examples, the adaptor 8020 may be provided outside of the tube and/or surrounding the tube. In this example, the first and second circuit elements are provided on the external surface of the tube and/or the tube connector.

The first and second circuit elements in the adapter allow for the sensing circuit in the humidifier to determine the type of tube connected to the dock 6050. This is different from the example in FIG. 10A, where characteristics of circuitry including the heating element and/or the sensor (e.g., provided in the tube) are used to determine the type of type connected to the system. Because of that, the value of the first and second circuit elements in this example of a passive tube needs to be selected so that it is outside of the range of values that would be expected from first and second circuit elements of the active tube in FIG. 10A. As would be discussed below, the specific electrical characteristics (i.e., resistance) of the NTC element has to be considered in working environment where it may spread over a broad range of values.

FIG. 12 shows a schematic view of a tube NTC resistance variations over different temperatures for a 100 k thermistor (usually used with a 19 mm heated tube) and a 10 k thermistor (usually used with a 15 mm heated tube). The 100 k thermistor and a 10 k thermistor may correspond to the thermistor that may be included in the second circuit element 8024 shown in FIG. 10A. The present technology is based on using the resistor connected to NTC terminals of an adaptor, which is distinctly different from that of the real NTC resistances at legitimate areas of operation. As seen in FIG. 12, the area between approximately 27 Kohm and 51K is not used by the 10 k and 100 k NTC during normal operation, so the resistor used in the tube (or adaptor as discussed below) can be selected to be at 36K or thereabout. Accordingly, when a tube with an adaptor having a second circuit element 8024 resistance value of 36 k is connected, the system will know that the tube is not the 15 mm tube using the 10 k thermistor nor the 19 mm tube using the 100 k thermistor. Whilst such atypical value resistance was described above as indicating the use of a passive tube with an adaptor, the specific resistance of one or more electrical pins may be used to indicate a variety of other parameters associated with the tube or even the mask, in a tube-mask system. Such parameters may include the presence or absence of HME in the tube/mask, the type of mask attached to the tube (nasal or full face) etc.

To reduce the possibility of the false detection (in case, for example, when 15 mm heated tube is exposed to the sun and gets heated to 50° C. and then gets immediately connected to the dock), the first circuit element 8022 is used in the adapter, which connects the Heater+ and Heater−terminals together through the resistance of a predetermined value (e.g., approximately 1 kΩ). A 1 kΩ resistance can conduct maximum 24 mA of current (at 100% PWM) which is only dissipating 0.6 W power but is enough to be reliably measured by dock subsystem circuit.

Using two circuit elements (e.g., resistors) as described above in the adapter practically eliminates the possibility of misdetection of the connected tube while keeping the system safe. Using the resistors provides for a low cost identification system with accurate identification. Other circuit elements (e.g., resistors, capacitors etc.) may be provided in parallels and/or series with the first and/or second circuit elements to provide characteristics that are distinct from characteristics of other circuits used for identification.

FIG. 13 shows a schematic view of a dock and a tube connection in accordance with another form of the present technology. The example shown in FIG. 13 is similar to the example shown in FIG. 11, but only uses a single circuit element (e.g., 36K resistor) in the adapter to reduce the cost of the adapter. In this example, in addition to reducing the number of circuit elements, the number of connections in the adapter are also decreased. The reliability of the detection may be somewhat diminished, as the combination of 36K value of NTC and open circuit of the Heater wire may also represent the situation of either double fault in the tube (NTC partial crack on NTC wire+open circuit on heater wire) or the case of the contaminated NTC terminals with the passive tube connected mechanically via ISO taper.

FIG. 14 shows a dock and a tube connection in accordance with another form of the present technology. In this example, a part of the PWM which is provided to the heating elements, is "injected" into the NTC detection circuit. This signal is detected by the microcontroller via the comfort subsystem NTC measurement circuit. Because the detected signal is distinctly different from all standard modes of operation of other tubes discussed above, this example may present the best detectability. However, this configuration may be undesirable in some implementations because it uses the undesirable functional interaction between two different parts of the circuitry (+24 PWM heating and +3V3 NTC detection) that logically should not be functionally connected together.

While the above examples of the present technology have been described with reference to a four wire system, the examples are not so limited. The examples of the present technology may be applied to systems with other number of wires, e.g., two wires, three wires, or five or more wires.

Also, whilst the above embodiments were mostly described with respect to detecting the type (size) of tube attached to the system, the variation in electrical parameter values described in relation to FIGS. 10-14, may be used to not only indicate various parameters associated with the tube (e.g. the type (heated/non-heated) and size (15 mm or 19 mm)) but also of parameters associated with the mask used. For example, the variation in electrical parameters may be used to indicate one or more of the following mask parameters; the type of the mask attached to the tube (nasal or full face), the mask size (small, medium, large), the presence or absence of HME in the tube/mask etc.

5.8 Breathing Waveforms

FIG. 4 shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak −0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.9 Glossary

For the purposes of the present technology disclosure, in certain forms of the present technology, one or more of the following definitions may apply. In other forms of the present technology, alternative definitions may apply.

5.9.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, $g\text{-}f/cm^2$ and hectopascal. 1 $cmH_2O$ is equal to 1 $g\text{-}f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.9.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.9.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH$_2$O pressure.

As an example, an I-beam may comprise a different bending stiffness (resistance to a bending load) in a first direction in comparison to a second, orthogonal direction. In another example, a structure or component may be floppy in a first direction and rigid in a second direction.

5.9.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
  (i) Flattened: Having a rise followed by a relatively flat portion, followed by a fall.
  (ii) M-shaped: Having two local peaks, one at the leading edge, and one at the trailing edge, and a relatively flat portion between the two peaks.
  (iii) Chair-shaped: Having a single local peak, the peak being at the leading edge, followed by a relatively flat portion.
  (iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
  (i) a 30% reduction in patient breathing for at least 10 seconds plus an associated 4% desaturation; or
  (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.9.3 Ventilation

Adaptive Servo-Ventilator (ASV): A servo-ventilator that has a changeable, rather than fixed target ventilation. The changeable target ventilation may be learned from some characteristic of the patient, for example, a respiratory characteristic of the patient.

Backup rate: A parameter of a ventilator that establishes the minimum breathing rate (typically in number of breaths per minute) that the ventilator will deliver to the patient, if not triggered by spontaneous respiratory effort.

Cycled: The termination of a ventilator's inspiratory phase. When a ventilator delivers a breath to a spontaneously breathing patient, at the end of the inspiratory portion of the breathing cycle, the ventilator is said to be cycled to stop delivering the breath.

Expiratory positive airway pressure (EPAP): a base pressure, to which a pressure varying within the breath is added to produce the desired mask pressure which the ventilator will attempt to achieve at a given time.

End expiratory pressure (EEP): Desired mask pressure which the ventilator will attempt to achieve at the end of the expiratory portion of the breath. If the pressure waveform template $\Pi(\Phi)$ is zero-valued at the end of expiration, i.e. $\Pi(\Phi)=0$ when $\Phi=1$, the EEP is equal to the EPAP.

Inspiratory positive airway pressure (IPAP): Maximum desired mask pressure which the ventilator will attempt to achieve during the inspiratory portion of the breath.

Pressure support: A number that is indicative of the increase in pressure during ventilator inspiration over that during ventilator expiration, and generally means the difference in pressure between the maximum value during inspiration and the base pressure (e.g., PS=IPAP−EPAP). In some contexts pressure support means the difference which the ventilator aims to achieve, rather than what it actually achieves.

Servo-ventilator: A ventilator that measures patient ventilation, has a target ventilation, and which adjusts the level of pressure support to bring the patient ventilation towards the target ventilation.

Spontaneous/Timed (S/T): A mode of a ventilator or other device that attempts to detect the initiation of a breath of a spontaneously breathing patient. If however, the device is unable to detect a breath within a predetermined period of time, the device will automatically initiate delivery of the breath.

Swing: Equivalent term to pressure support.

Triggered: When a ventilator delivers a breath of air to a spontaneously breathing patient, it is said to be triggered to do so at the initiation of the respiratory portion of the breathing cycle by the patient's efforts.

5.9.4 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Functional dead space:

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.10 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.11 REFERENCE SIGNS LIST

| Feature Item | Number |
| --- | --- |
| patient | 1000 |
| bed partner | 1100 |
| patient interface | 3000 |
| seal-forming structure | 3100 |
| plenum chamber | 3200 |
| structure | 3300 |
| vent | 3400 |
| connection port | 3600 |
| forehead support | 3700 |
| RPT device | 4000 |
| main panel | 4010 |
| front panel | 4012 |
| side panel | 4014 |
| chassis | 4016 |
| pneumatic block | 4020 |
| air filter | 4110 |
| inlet air filter | 4112 |
| outlet air filter | 4114 |
| muffler | 4120 |
| inlet muffler | 4122 |
| muffler | 4124 |
| pressure generator | 4140 |
| blower | 4142 |
| motor | 4144 |
| anti-spill back valve | 4160 |
| tube | 4170 |
| air circuit | 4171 |
| supplemental oxygen | 4180 |
| electrical components | 4200 |
| PCBA | 4202 |
| power supply | 4210 |
| input device | 4220 |
| central controller | 4230 |
| clock | 4232 |
| therapy device controller | 4240 |
| protection circuits | 4250 |
| memory | 4260 |
| sensors/transducers | 4270 |
| pressure sensor | 4272 |
| flow rate sensor | 4274 |
| motor speed transducer | 4276 |
| data communication interface | 4280 |
| remote external communication network | 4282 |
| local external communication network | 4284 |
| remote external device | 4286 |
| local external device | 4288 |
| output device | 4290 |
| display driver | 4292 |

-continued

5.11 REFERENCE SIGNS LIST

| Feature Item | Number |
|---|---|
| display | 4294 |
| algorithms | 4300 |
| pre-processing module | 4310 |
| pressure compensation algorithm | 4312 |
| vent flow rate estimation algorithm | 4314 |
| leak flow rate estimation algorithm | 4316 |
| respiratory flow rate estimation algorithm | 4318 |
| therapy engine module | 4320 |
| phase determination algorithm | 4321 |
| waveform determination algorithm | 4322 |
| ventilation determination algorithm | 4323 |
| inspiratory flow limitation determination algorithm | 4324 |
| apnea/hypopnea determination algorithm | 4325 |
| snore determination algorithm | 4326 |
| airway patency determination algorithm | 4327 |
| target ventilation determination algorithm | 4328 |
| therapy parameter determination algorithm | 4329 |
| therapy control module | 4330 |
| methods | 4340 |
| dock connector | 4600 |
| humidifier | 5000 |
| humidifier reservoir | 5110 |
| humidifier transducer | 5210 |
| pressure transducers | 5212 |
| air flow rate transducer | 5214 |
| temperature transducers | 5216 |
| humidity sensor | 5218 |
| heating element | 5240 |
| humidifier controller | 5250 |
| central humidifier controller | 5251 |
| heating element controller | 5252 |
| air circuit controller | 5254 |
| humidifier | 6000 |
| reservoir dock | 6050 |
| dock | 6050 |
| heater plate | 6080 |
| heating element | 6085 |
| water reservoir | 6100 |
| contact assembly | 6800 |
| adapter | 8020 |
| circuit element | 8022 |
| circuit element | 8024 |
| heater wire | 9010 |
| resistors | 9010 |
| resistors | 9012 |
| resistors | 9020 |
| resistors | 9022 |
| sensor | 9030 |

The invention claimed is:

1. An apparatus for providing a supply of humidified pressurized breathable gas to a patient interface, the apparatus comprising: a flow generator configured to pressurize a supply of breathable gas; a humidifier configured to provide water vapour to humidify the supply of pressurized breathable gas; a heated tube configured to be connectable to the humidifier to heat and deliver the humidified supply of breathable gas to the patient interface; a sensor configured to measure a property of the humidified supply of breathable gas in the heated tube; a controller configured to control power provided to the heated tube and control operation of the flow generator; a set of low pass filters coupled between the sensor and the controller and a set of high pass filters coupled between the sensor and ground; and wherein the power supplied to the heated tube comprises a pulse width modulated power signal and at least a set of low pass filters is configured to filter frequencies near the frequencies of the pulse width modulated power signal and frequencies higher than the frequencies of the pulse width modulated power signal.

2. The apparatus according to claim 1, wherein the apparatus comprises two high pass filters, one connected between each respective terminal of the sensor and the ground.

3. The apparatus according to claim 1, wherein the apparatus comprises a set of low pass filters coupled between the sensor and the controller and the set of high pass filters coupled between the sensor and the ground.

4. The apparatus according to claim 1, wherein the sensor is coupled to a sensor power source, wherein the controller is configured to:
control the sensor power source to provide intermittently power to the sensor in order to detect a connection of the heated tube; and
keep the sensor power source on, when it is detected that the heated tube is connected to the humidifier.

5. The apparatus according to claim 1, comprising the set of low pass filters, each low pass filter including an active component.

6. The apparatus according to claim 1, comprising the set of high pass filters, each including an active component.

7. The apparatus according to claim 1, wherein the heated tube includes a set of sensor wires extending along the length of the heated tube, each of the sensor wires coupled to the sensor and the controller.

8. The apparatus according to claim 7, comprising the set of high pass filters, wherein a first high pass filter of the set of high pass filters is coupled between ground and one of the sensor wires, and a second high pass filter of the set of high pass filters is coupled between ground and another one of the sensor wires.

9. The apparatus according to claim 7, comprising the set of low pass filters, wherein a first low pass filter of the set of low pass filters is coupled between the controller and one of the sensor wires, and a second low pass filter of the set of low pass filters is coupled between the controller and another one of the sensor wires.

10. The apparatus according to claim 1, wherein the controller includes a sensing circuit configured to detect voltage and/or current changes, and the controller is configured to control power provided to the heated tube based on the detected voltage and/or current changes.

11. The apparatus according to claim 1, wherein the heated tube includes a pair of helically wound heating wires around an axis of the heated tube and extending along the length of the heated tube, configured to heat air in the heated tube, and coupled to ground and a heater control circuit included in the controller.

12. The apparatus according to claim 11, comprising the set of high pass filters, wherein the heated tube includes a set of sensor wires extending along the length of the heated tube, each of the sensor wires coupled to the sensor and the controller, and a first high pass filter of the set of high pass filters is coupled between the ground and one of the sensor wires, and a second high pass filter of the set of high pass filters is coupled between the ground and another one of the sensor wires.

13. The apparatus according to claim 1, comprising the set of high pass filters, wherein the set of high pass filters is provided in the heated tube.

14. The apparatus according to claim 1, comprising the set of low pass filters, wherein the set of low pass filters is provided in the heated tube.

15. The apparatus according to claim 1, comprising the set of low pass filters, wherein the set of low pass filters is provided outside of the heated tube.

16. An apparatus for treating a respiratory disorder in a patient, the apparatus comprising: a motor-blower configured to generate a supply of air at a positive pressure relative to ambient pressure; a humidifier configured to provide water vapour to humidify the supply of pressurized air; a tube removably connected to the humidifier on one end and a patient interface on another end, the tube including one or more heating wires extending along the length of the tube and configured to heat the humidified supply of breathable air passed though the tube and one or more sensor wires extending along the length of the tube and coupled to a sensor configured to measure a property of the humidified supply of breathable gas in the tube; a controller including circuitry configured to control power provided to the one or more heating wires, control operation of the motor-blower, control operation of the humidifier; a set of low pass filters coupled between the sensor wires and the controller, and a set of high pass filters coupled between the sensor wire and the ground; and wherein the power provided to the heating wires comprises a pulse width modulated power signal and the one or more low pass filters are configured to filter frequencies near the frequencies of the pulse width modulated power signal and frequencies higher than the frequencies of the pulse width modulated power signal.

17. The apparatus according to claim 16, wherein the apparatus comprises two heating wires, two sensor wires, a set of low pass filters coupled between the sensor wires and the controller, and a set of high pass filters coupled between the sensor wire and the ground.

* * * * *